United States Patent
Chang et al.

(10) Patent No.: US 9,642,830 B2
(45) Date of Patent: May 9, 2017

(54) USE OF STING AGONISTS TO TREAT HEPATITIS B VIRUS INFECTION

(71) Applicant: DREXEL UNIVERSITY, Philadelphia, PA (US)

(72) Inventors: Jinhong Chang, Chalfont, PA (US); Fang Guo, Doylestown, PA (US); Timothy M. Block, Doylestown, PA (US); Ju-Tao Guo, Lansdale, PA (US)

(73) Assignee: Drexel University, Philadelphia, PA (US)

(*) Notice: Subject to any disclaimer, the term of this patent is extended or adjusted under 35 U.S.C. 154(b) by 0 days.

(21) Appl. No.: 15/028,813

(22) PCT Filed: Oct. 21, 2014

(86) PCT No.: PCT/US2014/061536
§ 371 (c)(1),
(2) Date: Apr. 12, 2016

(87) PCT Pub. No.: WO2015/061294
PCT Pub. Date: Apr. 30, 2015

(65) Prior Publication Data
US 2016/0256434 A1    Sep. 8, 2016

Related U.S. Application Data

(60) Provisional application No. 61/893,526, filed on Oct. 21, 2013.

(51) Int. Cl.
| | | |
|---|---|---|
| *A61K 31/35* | (2006.01) | |
| *A61K 31/352* | (2006.01) | |
| *A61K 31/473* | (2006.01) | |
| *C12Q 1/70* | (2006.01) | |
| *G01N 33/50* | (2006.01) | |

(52) U.S. Cl.
CPC .......... *A61K 31/352* (2013.01); *A61K 31/473* (2013.01); *C12Q 1/706* (2013.01); *G01N 33/5067* (2013.01); *C12Q 2600/136* (2013.01); *G01N 2333/02* (2013.01)

(58) Field of Classification Search
CPC ...................................................... A61K 31/35
USPC ........................................................ 514/456
See application file for complete search history.

(56) References Cited

U.S. PATENT DOCUMENTS

2012/0184578 A1* 7/2012 Teow ................... A61K 31/355
                                                                    514/297
2013/0039933 A1    2/2013 Barber

OTHER PUBLICATIONS

Prantner, D. et al., "5,6-Dimethylxanthenone-4-acetic Acid (DMXAA) Activates Stimulator of Interferon Gene (STING)-dependent Innate Immune Pathways and Is Regulated by Mitochondrial Membrane Potential," J. Biol. Chem., 2012, vol. 287, No. 47, pp. 39776-39788.

* cited by examiner

*Primary Examiner* — Raymond Henley, III
(74) *Attorney, Agent, or Firm* — Saul Ewing LLP; Kathryn Doyle; Domingos J. Silva

(57) ABSTRACT

The invention includes methods of treating a subject having hepatitis B viral (HBV) infection. In certain embodiments, the method of the invention comprises stimulating the innate cytokine response in macrophages, dendritic cells and/or liver non-parenchymal cells with small molecular STING agonists, thus suppressing HBV replication in hepatocytes. In other embodiments, the method of the invention can be used to treat chronic HBV infections. The invention further provides methods of identifying compounds useful in treating HBV infection in a subject.

27 Claims, 18 Drawing Sheets

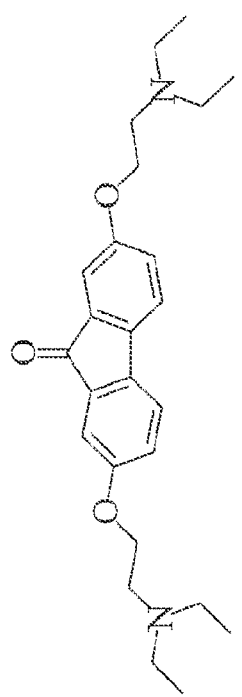
Tilorone
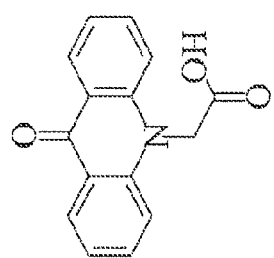
CMA
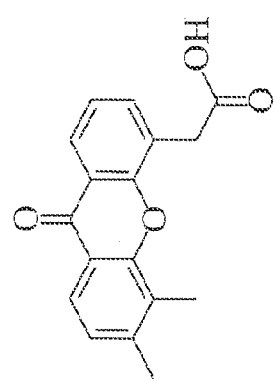
DMXAA
FIG. 3A

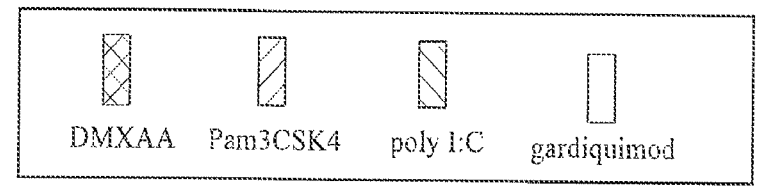
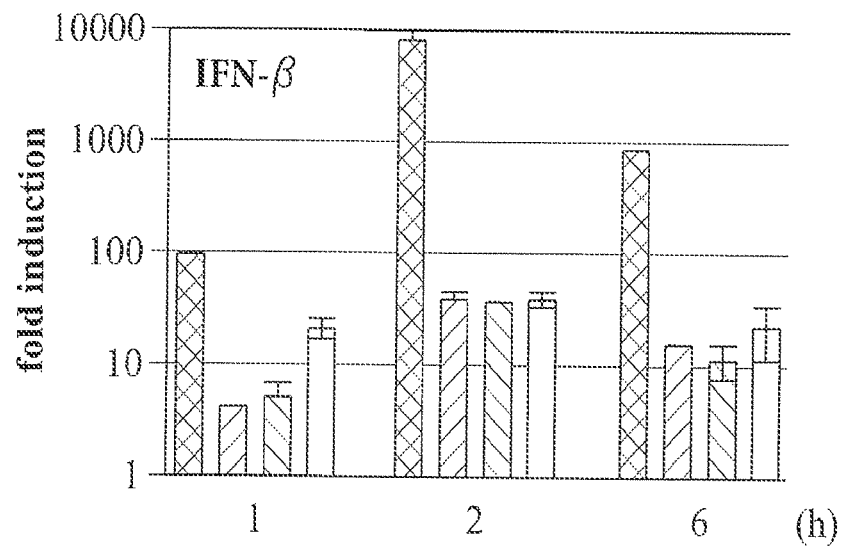
FIG. 6A
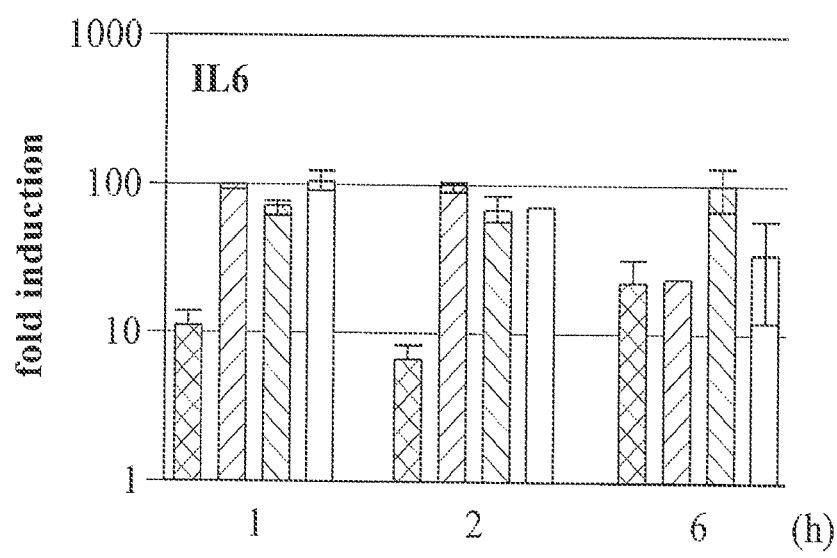
FIG. 6B

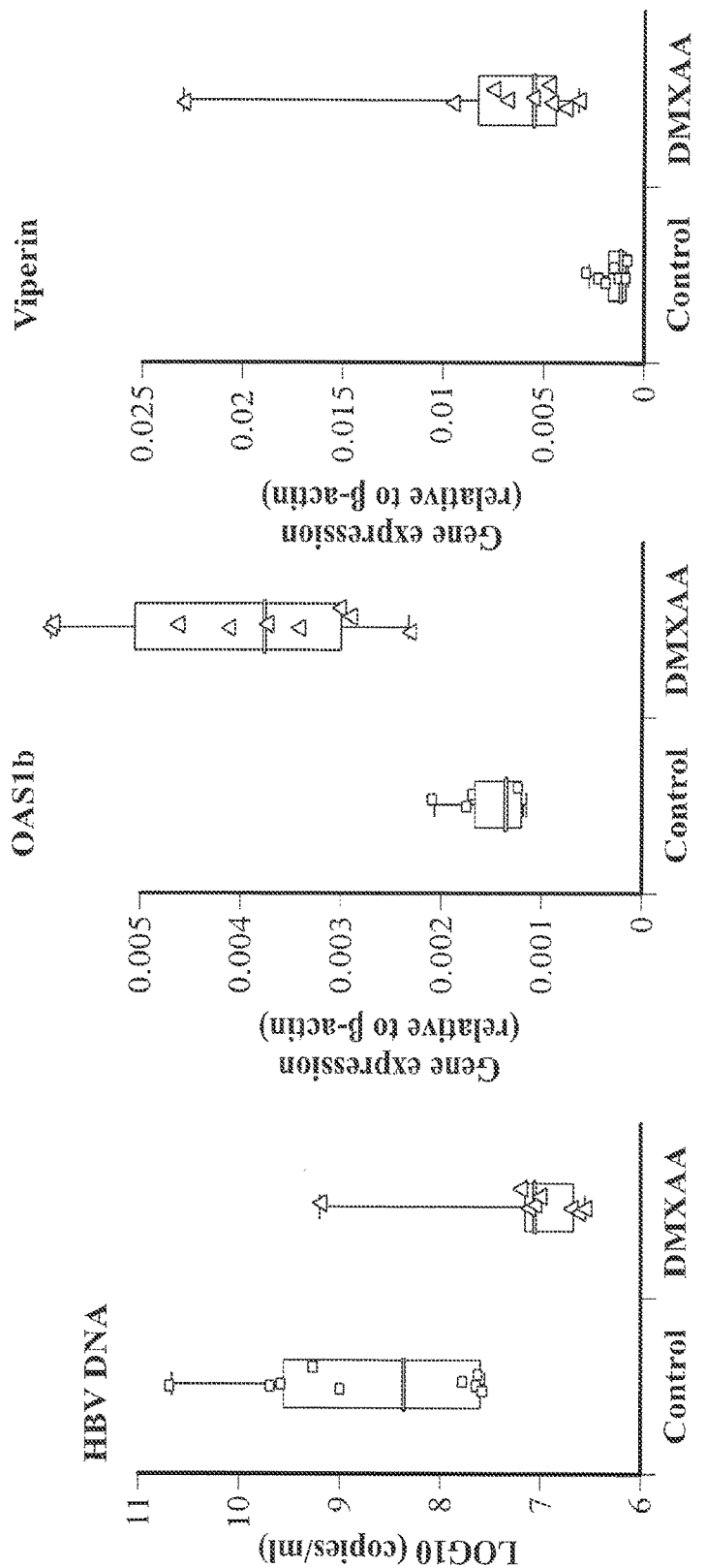

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcagctgcag cagttccaga a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctaggagat cttcagtttc g                                              21

<210> SEQ ID NO 3
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 3
ggctttcgga aaattcctat g                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccctacga accactgaac                                                20

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcaatcagct acataacaac tcgagttgtt atgtagctga ttga                     44
```

USE OF STING AGONISTS TO TREAT HEPATITIS B VIRUS INFECTION

CROSS-REFERENCE TO RELATED APPLICATIONS

This application is a 35 U.S.C. 371 national phase application of International Application No. PCT/US2014/061536, filed Oct. 21, 2014, and published under PCT Article 21(2) in English, which claims priority to U.S. Provisional Patent Application No. 61/893,526, filed Oct. 21, 2013, all of which disclosures are hereby incorporated herein by reference in their entireties.

STATEMENT REGARDING FEDERALLY SPONSORED RESEARCH OR DEVELOPMENT

This invention was made with government support under Contract No. AI104636 awarded by the National Institutes of Health. The government has certain rights in the invention.

TECHNICAL FIELD

This disclosure provides methods of treating a subject having hepatitis B viral (HBV) infection. More specifically, disclosed herein are methods of stimulating the innate cytokine response in macrophages, dendritic cells and/or liver non-parenchymal cells with small molecular agonists of STING to suppress HBV replication in hepatocytes. The disclosed methods are especially suitable for use in the treatment of chronic HBV infections. Also disclosed herein are methods of identifying compounds useful in the treatment of HBV infection.

BACKGROUND

Viral infections are promptly recognized by host pattern recognition receptors (PRRs), such as Toll-like receptors (TLRs), RIG-I-like receptors (RLR) and many others, which activate cellular responses leading to production of type I interferons (IFN), proinflammatory cytokines and chemokines. This early cytokine response not only limits virus replication and spreading, but also orchestrates the onset of more specific and powerful adaptive immune response, which ultimately eliminates the viruses. The essential role of PRR-mediated innate cytokine response in defending viral infection is well illustrated by the fact that humans and mice deficient in the genes encoding PRRs or their signaling components are vulnerable to viral infections.

In order to establish infection, pathogenic viruses have evolved multiple mechanisms to evade and/or countermeasure PRR-mediated innate immune response. In fact, failure or improper activation of PRR-mediated cytokine response is frequently observed in many chronic viral infections, including chronic hepatitis B, for which the current antiviral therapy with viral DNA polymerase inhibitors fails to provide a cure.

Hepatitis B virus (HBV) is a non-cytopathic hepadnavirus that chronically infects more than 350 million people worldwide. Chronic hepatitis B virus (HBV) infection is due to the failure of a host to mount a sufficient immune response to clear the virus. The outcomes and pathogenesis of HBV infection are largely determined by the nature and magnitude of host antiviral immune response, which is generally related to the age at the time of infection. While over 95% of adult-acquired infections are spontaneously cleared within 6 months by a vigorous and polyclonal HBV-specific T cell response, more than 90% of exposed neonates and approximately 30% of children aged 1-5 years develop chronic infection, which is associated with a weaker and often barely detectable viral specific T cell response.

Sustained suppression of viral replication with long-term nucleos(t)ide analogue therapy or through a finite-duration of pegylated alpha interferon (IFN-α) therapy has been associated with improvement of liver diseases, prevention of liver decompensation and reduction of hepatocellular carcinoma morbidity and mortality. However, HBV surface antigen (HBsAg) seroconversion, the hallmark of a successful immunologic response to HBV with complete and durable control of infection, or a "functional cure," is rarely achieved with the current therapies.

Although the antiviral efficacy of TLR and RLR agonists have been observed in HBV transgenic mice, as well as animals infected with WHV or DHBV, systemic administration of the PRR agonists in doses necessary to achieve antiviral effects is usually associated with significant adverse effects, due to the activation of a wide-spectrum of cellular response and massive production of pro-inflammatory cytokines.

SUMMARY OF THE INVENTION

Disclosed herein are methods of treating a subject having a hepatitis B viral infection, comprising administering an effective amount of a STING agonist to said subject.

Also provided are methods of identifying compounds useful in the treatment of hepatitis B virus infection comprising: treating liver resident dendritic cells, macrophages, nonparenchymal cells, or any combination thereof with a compound of interest; incubating the cells in a conditioned medium; removing the conditioned medium or a portion thereof from the treated cells; and incubating hepatitis B virus infected hepatocytes with the conditioned medium.

Methods of treating a subject having a hepatitis B virus infection, comprising: treating liver resident dendritic cells, macrophages, nonparenchymal cells, or any combination thereof with a compound of interest; incubating the cells in a conditioned medium; removing the conditioned medium or a portion thereof from the treated cells; and administering the conditioned medium or a portion thereof to said subject are also provided herein.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings:

FIG. 1, comprising

FIG. 2, comprising

FIG. 3, comprising FIGS. 3A-3D, represents: A) Structures of exemplary mouse IFN inducers; B) an exemplary analysis of AML cells treated directly with DMXAA (upper panel), CMA (middle panel), tilorone (lower panel) (Direct Treatment) or indirectly with 50% of conditioned media harvested from RAW264.7 cells treated with each compound for 12 h; C) an exemplary analysis of RAW264.7 and AML12HBV10 cells mock-treated or treated with 125 µM of DMXAA or 1 µg/ml of LPS; and D) and exemplary analysis of AML12HBV10 cells directly or indirectly treated with lower doses of DMXAA.

FIGS. 4A-4E, represents exemplary analysis of AML12HBV10 cells treated directly with DMXAA, poly I:C, Pam3CSK4 or indirectly with 50% of conditioned media harvested from RAW264.7 cells treated with DMXAA or TLR agonists. A) Intracellular HBV RNA was determined by Northern blot; B) HBV core protein was determined by Western blot; C) HBV capsids was determined by native agarose gel assay; D) capsid-associated HBV DNA was determined by a native agarose gel assay; and E) Cytoplasmic HBV core DNA was determined by Southern blot hybridization.

FIGS. 5A-5E, represents an exemplary Western blot analysis of RAW264.7 cells treated with A) 125 µM of DMXAA, B) 1 µg/ml of Pam3CSK4 (TLR1/2 agonist), C) 3 µM of gardiquimod (TLR7 agonist), D) 1 µg/ml of poly I:C (TLR3 agonist), or E) 1 µg/ml of LPS (TLR4 agonist) for the indicated times.

FIG. 6, comprising FIGS. 6A-6G, represent an exemplary RT-PCR analysis of RAW264.7 cells treated with 125 µM of DMXAA, 1 µg/ml of Pam3CSK4 (TLR1/2 agonist), 10 µg/ml of poly I:C (TLR3 agonist) or 3 µM of gardiquimod (TLR7 agonist) for the indicated times. Analysis of A) IFN-β, B) IL6, C) ILL D) IL10, E) TNF-α, F) IL12, and G) CXCL10. Data (mean±standard deviation, N=3) were expressed as fold induction of gene expression relative to untreated controls.

FIG. 7, comprising

FIG. 8, comprising

FIG. 9, comprising FIGS. 9A-9C, represents an exemplary in vivo analysis of DMXAA in HBV hydrodynamic mouse model. Seven days post hydrodynamic injection of HBV 1.3mer plasmid, mice were treated with a single 25 mg/kg dose of DMXAA or vehicle through intraperitoneal injection. A) 24 hours post treatment, HBV core DNA was extracted from livers and analyzed by a real-time PCR assay. Control group (10 mice) and treatment group (9 mice). Plots represent HBV DNA copies/ml from each animal after subtraction of the copies from input plasmid. mRNA levels of B) OAS1b and C) viperin from the livers of mice. All the data were presented in boxplots to indicate medians, inter-quartiles as well as ranges (min, max), and were statistically analyzed by student's t-test (P<0.05).

FIG. 10, comprising

DETAILED DESCRIPTION OF THE INVENTION

Figure 1A:
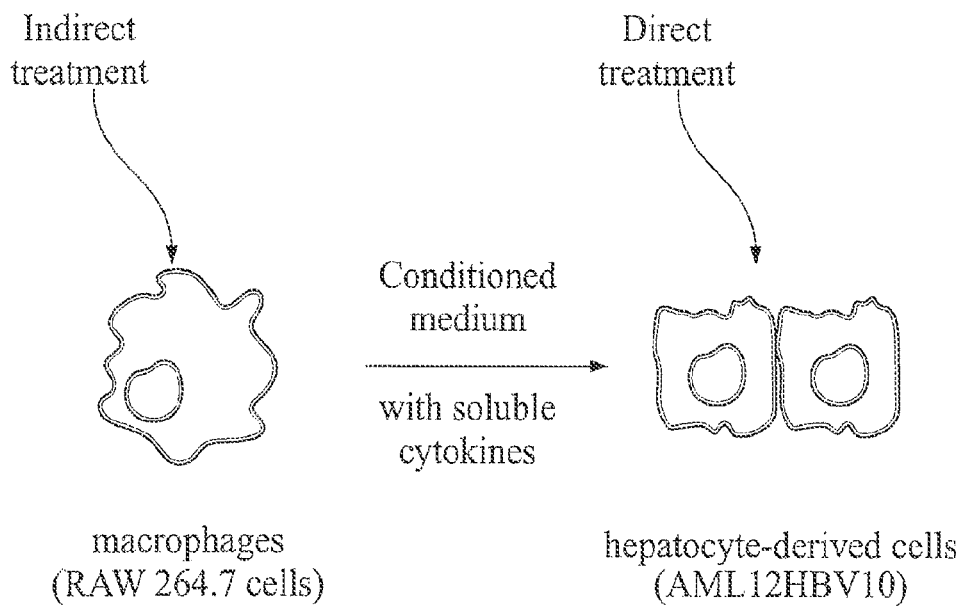
FIGS. 1A-1C, illustrates: A) an exemplary representation of the assay strategy; B) treatment of AML12HBV10 cells with TLR agonists (direct treatment) or media containing 50% of the conditioned media harvested from TLR agonist treated RAW264.7 cells (indirect treatment); and C) indirect treatment of AML12HBV10 cells with conditioned media harvested from TLR agonist treated RAW264.7 cells.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

The following abbreviations are used throughout the specification: HBV (hepatitis B virus infection); STING (stimulator of interferon genes); PRR (pattern recognition receptor); CMA (10-(carboxymethyl)-9(10H)acridone); DMXAA (5,6-dimethylxanthenone-4-acetic acid); hSTINGS162 (human STING with S162A mutation).

As used herein, "treating" and like terms refer to a reducing the severity and/or frequency of chronic HBV symptoms, eliminating HBV symptoms and/or the underlying cause of said symptoms, reducing the frequency or likelihood of HBV symptoms and/or their underlying cause, and improving or remediating damage caused, directly or indirectly, by HBV.

As used herein, "administering . . . to said patient" and similar terms indicate a procedure by which a STING agonist or conditioned medium or a portion thereof is provided to a patient such that target cells, tissues, or segments of the body of the subject are contacted with the active components from the conditioned medium. Suitable methods of administering a STING agonist or conditioned medium or a portion thereof include injection or oral delivery.

The term "subject" as used herein is intended to mean any animal, in particular, mammals. Although STING agonist induced inhibition of HBV replication in mice is exemplified herein, any type of mammal can be treated using the disclosed methods. Thus, the methods are applicable to human and nonhuman animals, although preferably used with mice and humans, and most preferably with humans. "Subject" and "patient" are used interchangeably herein.

The term "conditioned medium" as used herein refers to media that is harvested from cultured cells.

Provided herein are methods of treating a subject having a hepatitis B viral infection, comprising administering an effective amount of a STING agonist to said subject.

Those skilled in the art know that STING (stimulator of interferon genes) is the adaptor of multiple cytoplasmic DNA receptors and a pattern recognition receptor (PRR) recognizing bacterial second messengers cyclic di-adenosine monophosphate (c-di-AMP) and cyclic di-guanosine monophosphate (c-di-GMP). Cytosolic DNA binds to cyclic guanosine monophosphate-adenosine monophosphate (cGAMP) synthase (cGAS), to produce cyclic guanosine monophosphate-adenosine monophosphate (cyclic GMP-AMP, or cGAMP), which subsequently binds to and activates the adaptor protein STING and induces IFNs. STING comprises five putative transmembrane regions, predominantly resides in the endoplasmic reticulum, and is able to activate both NF-kappaB and IRF3 transcription pathways to induce expression of type I interferon (IFN-alpha and IFN-beta) and exert a potent anti-viral state following expression.

The STING agonist can stimulate an innate cytokine response in macrophages, dendritic cells, liver non-parenchymal cells, or any combination thereof. Thus, in some embodiments, the STING agonist can stimulate an innate cytokine response in macrophages. In other embodiments, the STING agonist can stimulate an innate cytokine response in dendritic cells. In other embodiments, the STING agonist can stimulate an innate cytokine response in liver non-parenchymal cells. In yet other embodiments, the STING agonist can stimulate an innate cytokine response in any combination of the above listed cells.

The STING agonist stimulated innate cytokine response is mediated through cytokines. In some embodiments, for example, the innate cytokine response can be mediated through type 1 interferon.

Suitable STING agonists for use in the disclosed methods include, but are not limited to, flavonoids. In some embodiments, the STING agonist can comprise a flavonoid. In other embodiments, the STING agonist can consist of a flavonoid. Suitable flavonoids include, but are not limited to, 10-(carboxymethyl)-9(10H)acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof. In some aspects, the STING agonist can be 10-(carboxymethyl)-9(10H)acridone (CMA). In some aspects, the STING agonist can be 5,6-Dimethylxanthenone-4-acetic acid (DMXAA). In some aspects, the STING agonist can be methoxyvone. In some aspects, the STING agonist can be 6,4'-dimethoxyflavone. In some aspects, the STING agonist can be 4'-methoxyflavone. In some aspects, the STING agonist can be 3',6'-dihydroxyflavone. In some aspects, the STING agonist can be 7,2'-dihydroxyflavone. In some aspects, the STING agonist can be daidzein. In some aspects, the STING agonist can be formononetin. In some aspects, the STING agonist can be retusin 7-methyl ether. In some aspects, the STING agonist can be xanthone. In some aspects, the STING agonist can be any combination of the above flavonoids. Thus, for example, in some embodiments the flavonoid comprises DMXAA.

Administration of a STING agonist to a subject having HBV can suppress HBV replication in infected hepatocytes. For example, in some embodiments, the STING agonist can reduce hepatitis B virus capsid levels.

Also provided herein are methods of identifying compounds useful in the treatment of hepatitis B virus infection. A cell culture system has been established for identifying compounds that are useful in the treatment of HBV infection. As illustrated in FIG. 1A, an exemplary cell culture system can comprise a mouse macrophage-hepatocyte coupled cell culture system for identification of compounds that activate cytokine response in macrophages, which in turn suppresses HBV replication in hepatocytes. Using this cell culture system, it has been demonstrated that STING agonists, for example DMXAA, induce a potent antiviral response that is primarily mediated by type I IFNs and suppresses HBV replication by reducing the virus capsids.

Thus, in some embodiments, the methods of identifying compounds useful in the treatment of HBV infection comprise: 1) treating liver resident dendritic cells, macrophages, nonparenchymal cells, or any combination thereof with a compound of interest; 2) incubating the cells in a conditioned medium; 3) removing the conditioned medium or a portion thereof from the treated cells; and 4) incubating hepatitis B virus infected hepatocytes with the conditioned medium.

In some aspects, the methods comprise treating liver resident dendritic cells with a compound of interest. In other aspects, the methods comprise treating macrophages with a compound of interest. In other aspects, the methods comprise treating nonparenchymal cells with a compound of interest. In yet other aspects, the methods comprise treating any combination of the above cell types with a compound of interest.

Conditions and media for culturing various cells types are known to one skilled in the art. Macrophages, for example, can be cultured in Dublecco's modified Eagle medium (DMEM) supplemented with fetal bovine serum (FBS). Accordingly, in some embodiments, conditioned media comprises DMEM with FBS that is harvested from cultured macrophages.

In some embodiments, the methods further comprise measuring hepatitis B virus replication. Numerous techniques are known in the art for measuring HBV replication including, but not limited to, measuring: cytoplasmic HBV core DNA replication intermediates (RC, DSL and SS) by Southern blot hybridization or total HBV core DNA by real time PCR; intracellular HBV RNA (pgRNA and mRNA specifying HBV envelope proteins) by Northern blot; HBV core protein by Western blot assay; HBV capsid and capsid associated viral DNA by a native agarose gel electrophoresis followed by transfer to a nitrocellulose membrane; capsid-associated HBV DNA by Southern blot hybridization; or any combination thereof.

In some embodiments, the treatment of the liver resident dendritic cells, macrophages, nonparenchymal cells, or any combination thereof can stimulate an innate cytokine immune response, which can suppress hepatitis B virus replication in hepatocytes. For example, the treating step can stimulate an innate cytokine immune response within the liver resident dendritic cells, macrophages, nonparenchymal cells, or any combination thereof, and release cytokines into the conditioned medium. In some aspects, the cytokines include but are not limited to Type I IFNs. The conditioned medium in turn can suppress hepatitis B replication in the infected hepatocytes.

Although hepatocytes are the primary host cells of HBV, hepatic non-parenchymal cells (NPCs) have been shown to play a critical role in priming an effective HBV-specific antiviral immunity. For instance, activation of hepatic macrophages induces the expression of a distinct profile of cytokines/chemokines that regulate the priming of successful immune response against HBV in the livers of mice.

Also provided herein are methods of treating a subject having a hepatitis B virus infection, comprising: 1) treating liver resident dendritic cells, macrophages, nonparenchymal cells, or any combination thereof with a compound of interest; 2) incubating the cells in a conditioned medium; 3) removing the conditioned medium or a portion thereof from the treated cells; and 4) administering the conditioned medium or a portion thereof to said subject.

In some aspects, the methods comprise treating liver resident dendritic cells with a compound of interest. In other aspects, the methods comprise treating macrophages with a compound of interest. In other aspects, the methods comprise treating nonparenchymal cells with a compound of interest. In yet other aspects, the methods comprise treating any combination of the above cell types with a compound of interest.

Compounds of interest for use in the present methods include, but are not limited to, one or more STING agonists. For example, in some embodiments, the STING agonist can comprise a flavonoid. Suitable flavonoids include, but are not limited to, 10-(carboxymethyl)-9(10H)acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof. In some aspects, the STING agonist can be 10-(carboxymethyl)-9(10H)acridone (CMA). In some aspects, the STING agonist can be 5,6-Dimethylxanthenone-4-acetic acid (DMXAA). In some aspects, the STING agonist can be methoxyvone. In some aspects, the STING agonist can be 6,4'-dimethoxyflavone. In some aspects, the STING agonist can be 4'-methoxyflavone. In some aspects, the STING agonist can be 3',6'-dihydroxyflavone. In some aspects, the STING agonist can be 7,2'-dihydroxyflavone. In some aspects, the STING agonist can be daidzein. In some aspects, the STING agonist can be formononetin. In some aspects, the STING agonist can be retusin 7-methyl ether. In some aspects, the STING agonist can be xanthone. In some aspects, the STING agonist can be any combination of the above flavonoids. Thus, for example, in some embodiments the flavonoid comprises DMXAA.

Liver resident dendritic cells, macrophages, and/or nonparenchymal cells for use in the disclosed methods can be obtained from any suitable source. Preferably, the liver resident dendritic cells, macrophages, and/or nonparenchymal cells are mammalian. In some aspects, the liver resident dendritic cells, macrophages, and/or nonparenchymal cells can be mouse cells. In some aspects, the liver resident dendritic cells, macrophages, and/or nonparenchymal cells can be human cells. Thus, in some embodiments, the liver resident dendritic cells, macrophages, nonparenchymal cells, or any combination thereof are human cells.

The liver resident dendritic cells, macrophages, and/or nonparenchymal can be wild type cells or can be modified cells. As used herein, "modified cells" refer to cells that contain non-native, non-wild type, mutant, or altered levels of DNA and/or proteins. In some embodiments, the human liver resident dendritic cells, macrophages, nonparenchymal cells, or any combination thereof are modified to express a mutant STING. In some embodiments, the mutant STING can be STING S162A.

Numerous techniques are known in the art for generating modified cells including, but not limited to, transfection or transformation. In some embodiments, the human liver resident dendritic cells, macrophages, nonparenchymal cells, or any combination thereof are transfected or transformed with a mutant STING prior to the treating step.

The liver resident dendritic cells, macrophages, and/or nonparenchymal cells can be from a number of suitable sources. In some aspects, the liver resident dendritic cells, macrophages, nonparenchymal cells, or any combination thereof are autologous cells. In other aspects, the liver resident dendritic cells, macrophages, nonparenchymal cells, or any combination thereof are allogenic cells. In yet other aspects, the liver resident dendritic cells, macrophages, nonparenchymal cells, or any combination thereof are cells from a different species.

EXAMPLES

Materials and Methods

Cell Culture

Murine macrophage cell line RAW264.7 (ATCC TIB-71) and GP2-293 cells (Clontech) were maintained in Dublecco's modified Eagle medium (DMEM) supplemented with 10% fetal bovine serum (FBS). AML12HBV10, an immortalized murine hepatocyte (AML12)-derived cell line supporting high level of HBV replication in a tetracycline (tet)-inducible manner, was maintained as described in Xu C, et al. Interferons accelerate decay of replication-competent nucleocapsids of hepatitis B virus. J Virol 2010; 84:9332-40, and Campagna M R, et al. Sulfamoylbenzamide Derivatives Inhibit the Assembly of Hepatitis B Virus Nucleocapsids. J Virol 2013.

Reagents

DMXAA, CMA and 2,7-Bis[2-(diethylamino)ethoxy]-9-fluorenone (tilorone) were purchased from Sigma-Aldrich. TLR1/2 agonist Pam3CSK4, TLR3 agonist poly I:C, TLR4 agonist lipopolysaccharide (LPS), and TLR7 agonist gardiquimod were from Invivogen. Recombinant murine IFN-α, IL-1, IL-6 and TNF-α were from PBL Interferon- Source. Antibody against carboxyl terminal 14 amino acid of HBV core protein was described previously in Xu C, et al. Interferons accelerate decay of replication-competent nucleocapsids of hepatitis B virus. J Virol 2010; 84:9332-40. Antibodies against β-actin and mouse IFNAR-1 were obtained from Sigma-Aldrich and Santa Cruz Biotechnology, respectively. Antibodies against mouse STING, TBK1, $S^{172}$-phosphorylated TBK1, IkBα, p38, phosphorylated-p38, JNK, phosphorylated-JNK, ERK, phosphorylated-ERK, were purchased from Cell Signaling Technology. Plasmids pTmcs-HBV1.3 and pCMV-SB were kind gifts of Dr. Francis V. Chisari (The Scripps Research Institute, La Jolla, Calif., USA).

Analyses of HBV DNA, RNA and Nucleocapsids

HBV core DNA extraction from AML12HBV10 cells as well as analyses by Southern blot hybridization and real-time PCR assays were as described previously in Xu C, et al. Interferons accelerate decay of replication-competent nucleocapsids of hepatitis B virus. J Virol 2010; 84:9332-40, and Campagna M R, et al. Sulfamoylbenzamide Derivatives Inhibit the Assembly of Hepatitis B Virus Nucleocapsids. J Virol 2013. Total cellular RNA was extracted using TRIzol reagent (Invitrogen). HBV RNA was analyzed by Northern blot hybridization with an $\alpha$-$^{32}$P-UTP-labeled full-length minus-stranded RNA probe. HBV capsid and capsid associated viral DNA was analyzed by a native agarose gel electrophoresis followed by transfer to a nitrocellulose membrane. HBV capsids were detected by probing the membrane with an antibody against HBV core protein followed by visualizing with LI-COR Odyssey system. Capsid-associated DNA was detected by hybridization with radioactively labeled HBV riboprobe.

Real-Time PCR and RT-PCR Assays

For cytokine gene expression analysis, total RNA was extracted using TRIzol reagent. cDNAs were synthesized using SuperScript III (Invitrogen). Quantitative real-time PCR analysis was performed using a LightCycler 480 II (Roche). Primers used in the RT-PCR assays are shown in Table 1. Primers used in realtime PCR to detect HBV DNA are also shown in Table 1.

TABLE 1

| Primer | Sense | Antisense |
|---|---|---|
| Human IFN-β | 5'-GCA GCT GCA GCA GTT CCA GAA-3' | 5'-GCT AGG AGA TCT TCA GTT TCG-3' |
| HBV DNA | 5'-GGC TTT CGG AAA ATT CCT ATG-3' | 5'-AGC CCT ACG AAC CAC TGA AC-3' |

Generation of STING Knockdown Cell Line

A plasmid expressing shRNA specifically targeting murine STING was constructed by inserting the following cDNA sequence into pRS vector (Origene): tcaatcagcta-cataacaactcgagttgttatgtagctgattga. A control plasmid expressing scrambled shRNA from pRS vector was purchased from Origene. Package of VSV G protein pseudotyped retroviruses in GP2-293 cells using pCMV/VSV-G and pRS vector-derived plasmid expressing a scrambled shRNA or STING specific shRNA was essentially as reported previously in Zhao X, et al. Interferon induction of IFITM proteins promotes infection by human coronavirus OC43. Proc Natl Acad Sci USA 2014. RAW264.7 cells were transduced with pseudotyped retroviruses expressing each of the shRNA, as previously described in Zhao X, et al.

Antiviral Efficacy of DMXAA in HBV DNA Hydrodynamic Mouse Model

Ten-week-old female NOD/SCID mice were purchased from Vital River Laboratory Animal Technology Co. Ltd. All experiments were conducted with Institutional Animal Care and Use Committee approval. To establish HBV hydrodynamic model, 13.5 µg of plasmid pTmcsHBV1.3 expressing 1.3mer HBV genome and 4.5 µg of pCMV-SB expressing the Sleeping Beauty transposase were injected through tail vein, according to procedures previously described. To test the efficacy of DMXAA in vivo, 7 days post injection, mice were treated with either DMXAA (in PBS with 7.5% sodium Bicarbonate) at 25 mg/kg or vehicle, via intraperitoneal injection. Mice were sacrificed 24 h after treatment. Intrahepatic HBV core DNA was extracted and quantified by using a real-time PCR assay. Intrahepatic total RNA was extracted and the interferon stimulated genes (ISGs) OAS1b and viperin mRNAs were determined by real-time RT-PCR assay. Weight of individual mouse was monitored before and 24 h after the treatment.

Example 1

Establishment of Cell Culture System to Evaluate PRR Agonist-Induced Antiviral Response Against HBV Unlike RIG-I-like receptors that are ubiquitously expressed in many types of somatic cells, expression of other PRRs, such as TLRs and cGAS, is usually restricted to macrophages, dendritic cells and a few other cell types. Due to the lack of expression or expression in a low amount of PRRs, such as TLRs, treatment of hepatocytes usually does not induce a robust cytokine response. For instance, direct treatment of hepatocytes with TLR agonists induces a negligible cytokine response. However, liver resident dendritic cells, macrophages (Kupffer cells) and other hepatic non-parenchymal cells (NPCs) express high levels of TLRs and thus respond to TLR agonists and produce inflammatory cytokines.

To screen small molecular PRR agonists for treatment of chronic hepatitis B, a cell-based assay mimicking the intrahepatic environment was developed. This unique cell culture system, depicted in FIG. 1A, mimics the condition in HBV infected livers. Specifically, mouse macrophages (RAW 264.7) were treated with testing compounds and the conditioned media of treated macrophages were then applied to immortalized mouse hepatocytes harboring HBV (AML12HBV10) to test the compound-induced antiviral cytokine response in macrophages.

Example 2

Figure 1B:
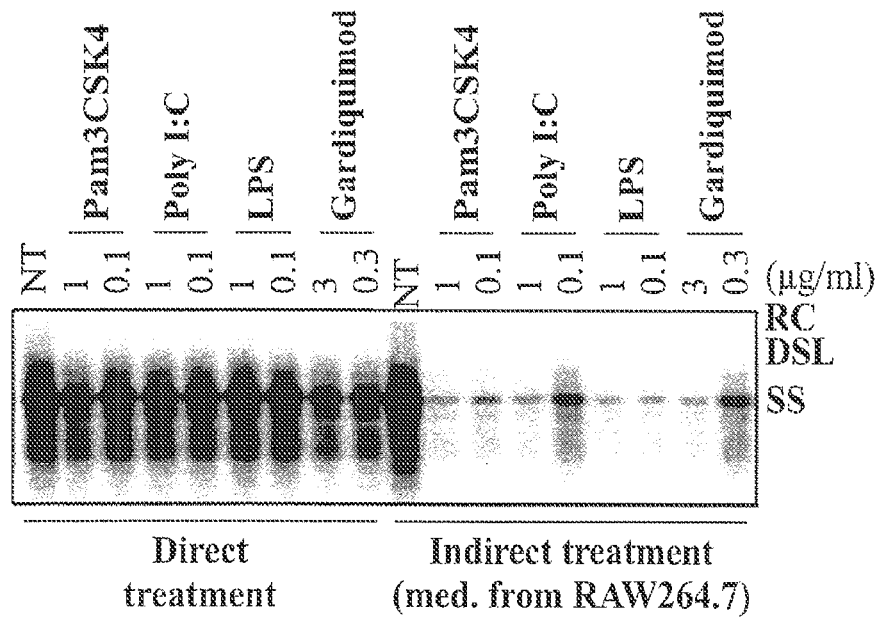

TLR Agonists Induce Strong Cytokine Response in Macrophages to Suppress HBV Replication in Hepatocytes: A Proof-of-Concept Experiment The assay system was first validated with known TLR agonists. AML12HBV10 cells were seeded in 12-well plate at density of 1×105 cell/well and cultured in the absence of tetracycline. Twenty-four hours later, the cells were treated with the indicated concentrations of TLR agonists (direct treatment) (FIG. 1B). Alternatively, AML cells were treated with media containing 50% of the conditioned media harvested from TLR agonists treated RAW264.7 cells (cultured in 12-well plate at density of 5×$10^5$ cell/well and treated with indicated concentrations of TLR agonists for 12 h) (indirect treatment). Cytoplasmic HBV core DNA was analyzed by Southern blot hybridization two days post treatment. RC, relaxed circular DNA. DSL, double-stranded linear DNA. SS, single-stranded DNA. NT, no treatment control, which were samples from mock treated AML cells (direct treatment control) or from AML12HBV10 cells treated with 50% media from mock treated RAW264.7 cells (indirect treatment control). As shown in FIG. 1B, while direct treatment of AML cells with agonists of TLR1/2 (Pam3CSK4), TLR3 (poly I:C), TLR4 (LPS) or TLR7 (gardiquimod) did not apparently inhibit HBV DNA replication, treatment of AML12HBV10 cells with the conditioned media harvested from TLR agonist-treated macrophages (indirect treatment) potently inhibited HBV DNA replication.

Figure 1C:
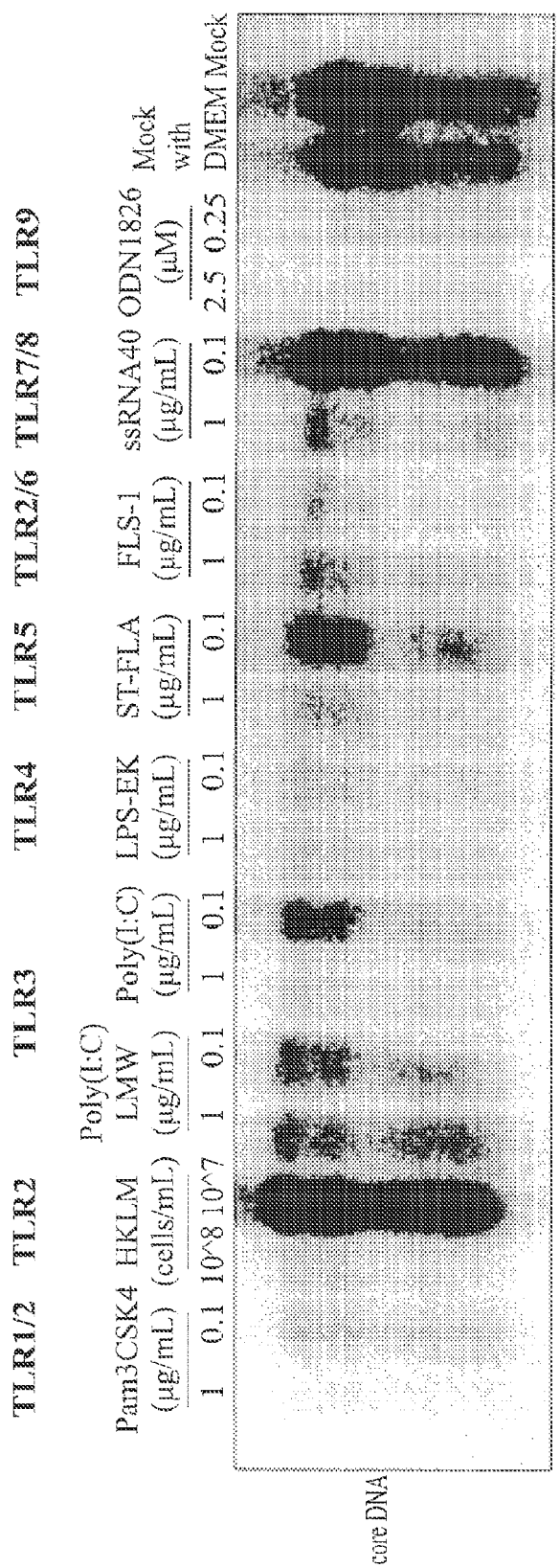

In another exemplary analysis, RAW264.7 cells in DMEM medium were seeded in 12-well plate at density of $5 \times 10^5$ cell/well overnight and treated with indicated doses of TLR agonists for 12 hrs (FIG. 1C). AMLHBV10 cells, grown in Dulbecco's Modification of Eagle's Medium (DMEM)/F12 medium with 1 µg/ml of tetracycline were seeded in 12-well plate at density of $1 \times 10^5$ cell/well for 1 day in absence of tetracycline to release HBV replication. Equal volume of supernatants from treated RAW264.7 cells were then transferred to AML12HBV10 cells. HBV core DNA was extracted from AML12HBV10 cells 2 days post treatment, and detected by Southern blot assay. Control AML12HBV10 cells received equal volume of either fresh DMEM medium (mock) or DMEM medium transferred from RAW264.7 cells mock treated for 12 hrs (mock with DMEM). Direct treatment of AML12HBV10 with a panel of TLR agonists did not have any effect on HBV DNA replication (data not shown). Culture of AML12HBV10 cells with conditioned media from macrophages treated with the TLR agonist, however, potently inhibited HBV DNA replication (FIG. 1C), presumably through induced secretion of soluble cytokines by the TLR agonists in macrophages.

Thus, although TLR agonists failed to directly activate an antiviral response in hepatocytes, TLR agonists induce macrophages to produce soluble factors that suppress HBV replication in hepatocytes.

Example 3

Figure 2A:
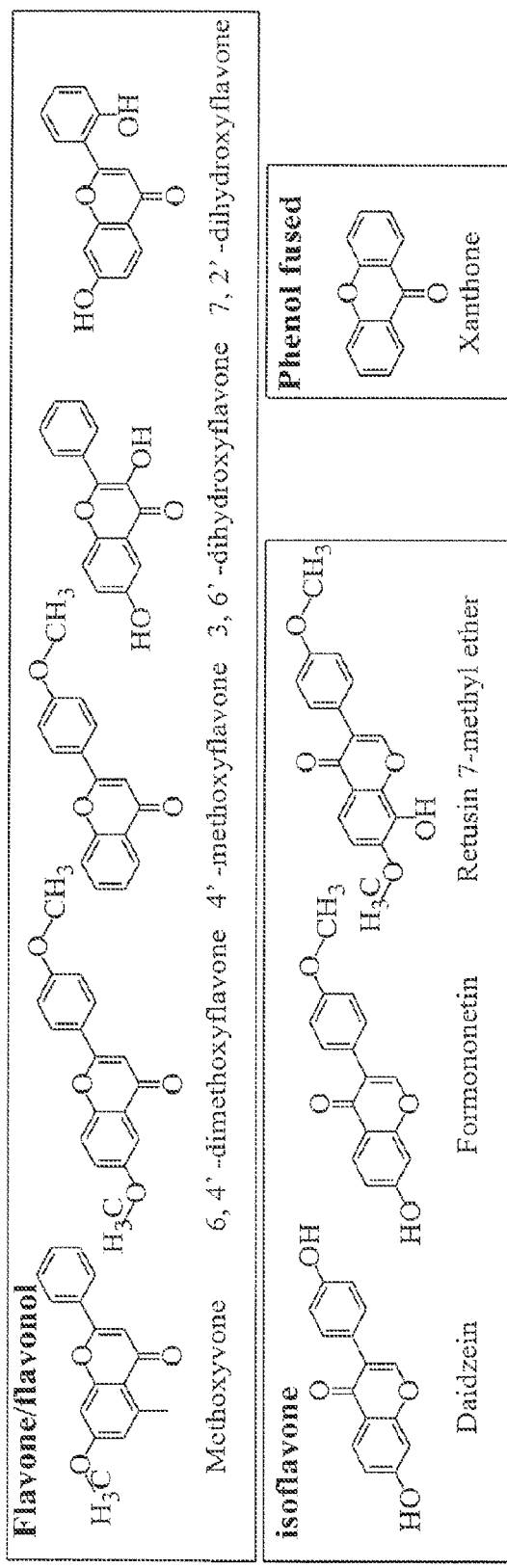
FIGS. 2A-2B, represents: A) structure of exemplary flavonoids identified from MicroSource library as innate immune enhancers; and B) analysis of AMLHBV10 cells treated directly with 7,2'-dihydroxyflavone compound, or indirectly with conditioned media from RAW264.7 cells treated with 7,2'-dihydroxyflavone compound.

Selected Flavoniods Induce Antiviral Response in Macrophages to Suppress HBV Replication in Hepatocytes The initial effort towards identification of molecules capable of activation of innate antiviral cytokine response in macrophages was focused on 2320 MicroSource compounds (MicroSource Discovery Systems, Inc.). This collection was a spectrum selection to represent the chemical class and structural diversity of synthetic and nature-derived compounds. Nine compounds were identified that enhance IFN-β promoter activity in TLR3-expressing HEK293 cells. Interestingly, all 9 of these compounds are flavones, flavonol or isoflavone, which belong to flavonoid structure family (FIG. 2A).

To test the representative compound 7,2' dihydroxyflavone, AMLHBV10 cells, cultured in absence of tetracycline for 1 day, were either directly treated with indicated doses (in µM) (FIG. 2B) of 7,2'-dihydroxyflavone compound, or indirectly treated for 2 days (by culturing with conditioned media transferred from RAW264.7 cells, which were treated with doses of the compound for 12 hrs). Intracellular HBV RNA was determined by Northern blot (ribosomal RNA served as loading control). HBV core protein was determined by Western blot assay using antibody against carboxyl terminal 14 amino acid of HBV core protein (β-actin served as loading control). HBV nucleocapsids were examined by a particle gel assay to detect both the intact nucleocapsids and capsid-associated HBV DNA. Encapsidated HBV (core DNA) replication intermediates (RC, DSL and SS) were determined by Southern blot assay.

Figure 2B:
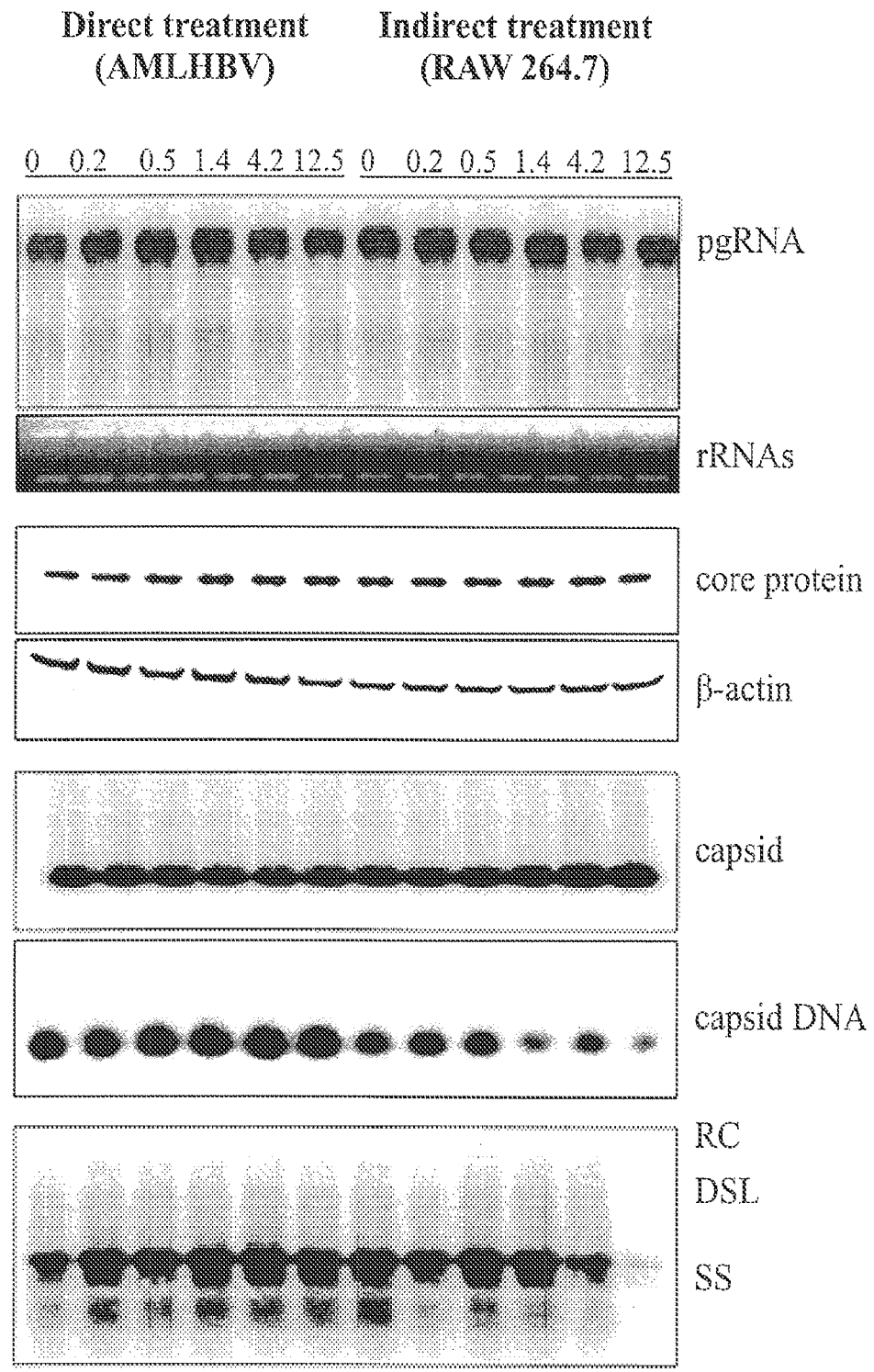

As demonstrated in FIG. 2B, treatment of RAW264.7 cells with a representative compound, 7,2' dihydroxyflavone, induces antiviral activity against HBV in AML12HBV10 cells. Without intending to be bound by theory, the observed response is most likely mediated by antiviral cytokines.

Example 4

Figure 3B:
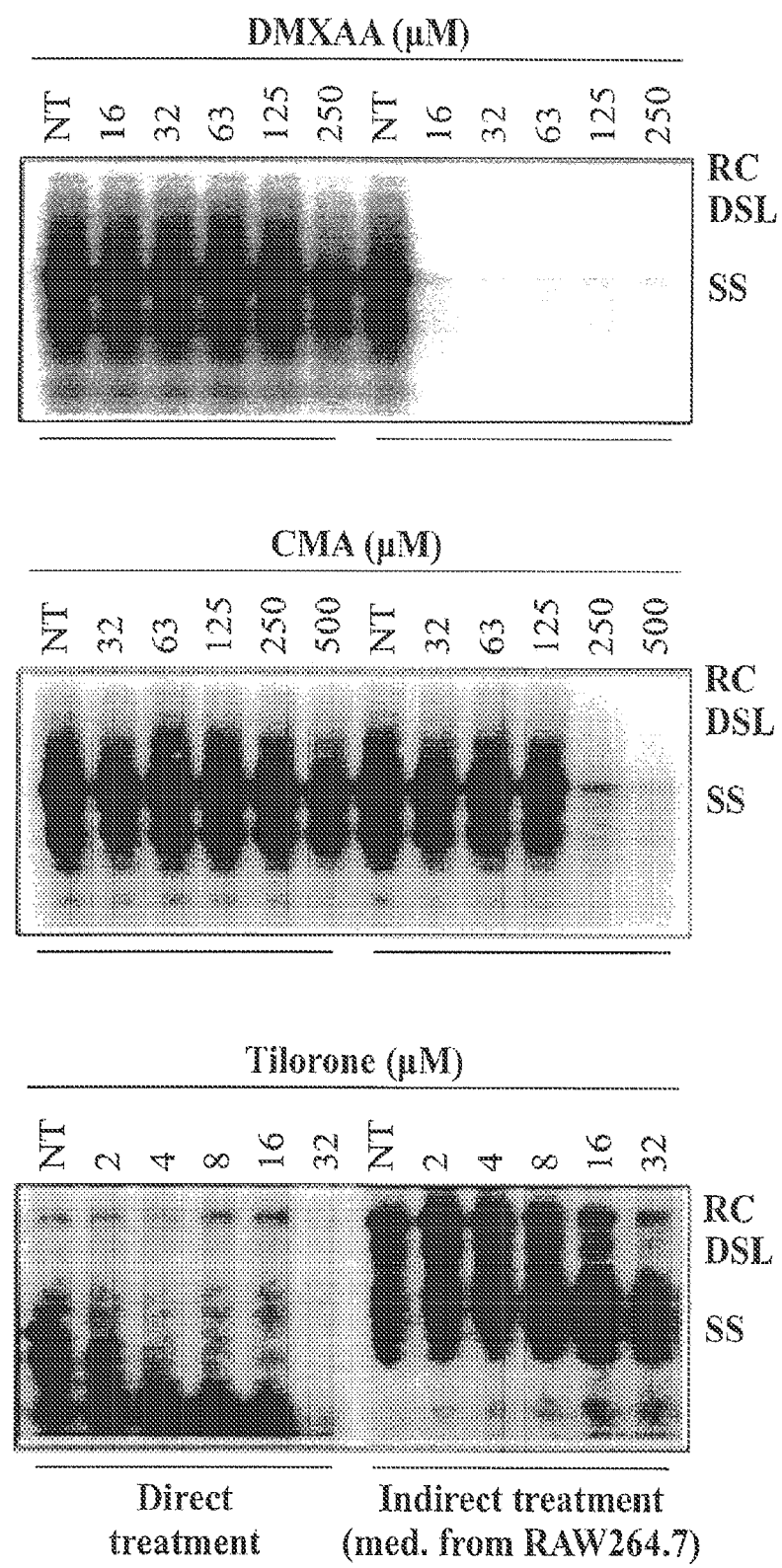
Figure 3C:
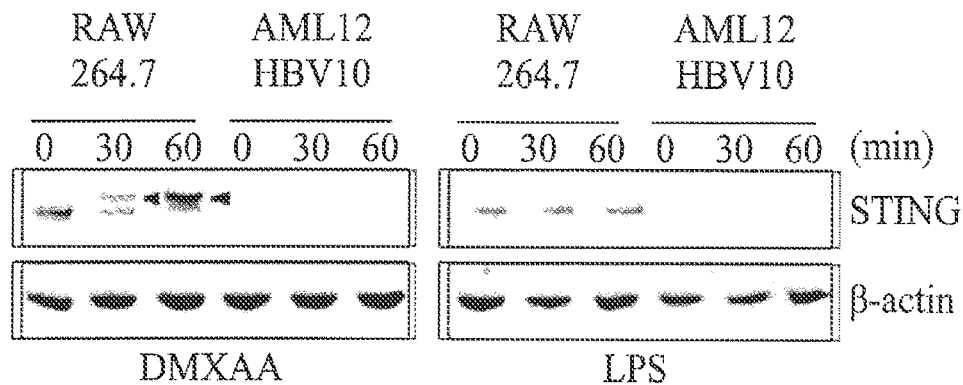
Figure 3D:
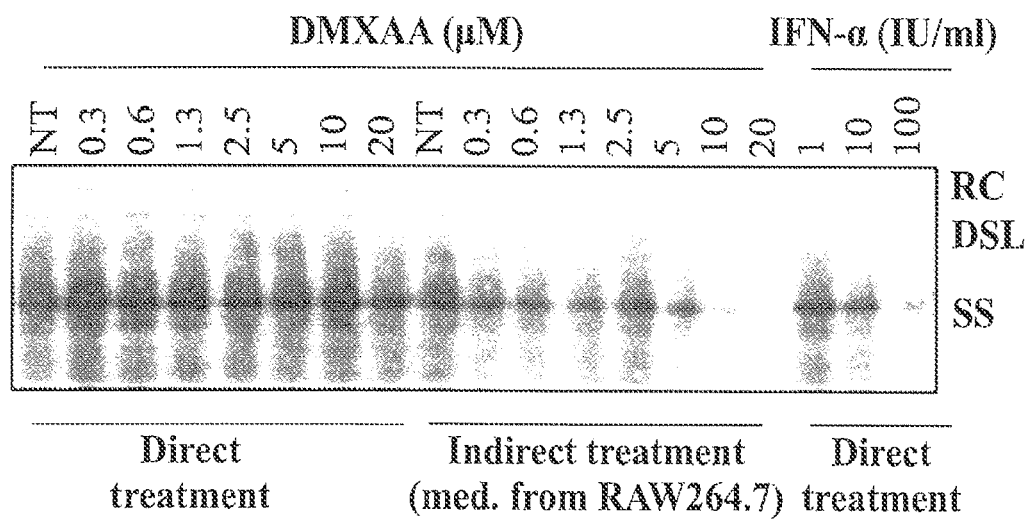

DMXAA-Induced Antiviral Response in Macrophages Potently Suppressed HBV Replication in Hepatocytes Using the assay system described above, 75 flavonoids in MicroSource compound collection (MicroSource Discovery Systems, Inc.) were tested again. The flavonoid, 7,2'-dihydroxyflavone demonstrated an indirect, but not direct, antiviral activity against HBV. Three flavonoid or flavonoied derived compounds identified as potent IFN response inducers in mice (tilorine, CMA and DMXAA) (FIG. 3A), were further analyzed. Briefly, AML12HBV10 cells, seeded and cultured as described in Example 2, FIG. 1B were treated for 2 days with the indicated concentrations of DMXAA (upper panel), CMA (middle panel), tilorone (lower panel) (Direct Treatment), or 50% of the conditioned media harvested from RAW264.7 cells (treated with each of the compound for 12 h) (Indirect Treatment). Cytoplasmic HBV core DNA was analyzed by Southern blot hybridization. NT controls were as described in FIG. 1B (FIG. 3B). RAW264.7 and AML12HBV10 cells were mock-treated or treated with 125 µM of DMXAA or 1 µg/ml of LPS for 30 and 60 min. Expression and activation of STING was determined by Western blot assay. Arrow heads indicate the shift in gel mobility, as a result of STING phosphorylation. β-actin served as loading control (FIG. 3C). AML12HBV10 cells cultured in the absence of tetracycline were directly or indirectly treated as described for panel B, except that lower doses of DMXAA were used. AML12HBV10 cells treated with the indicated concentrations of mouse alpha IFN (mIFN-α) for 2 days served as positive controls. Cytoplasmic HBV core DNA was analyzed by Southern blot hybridization (FIG. 3D).

While tilorine neither directly nor indirectly inhibited HBV replication, both CMA and DMXAA demonstrated a strong indirect anti-HBV activity (FIG. 3B). As shown in FIG. 3C, DMXAA, but not LPS, efficiently induces phosphorylation of STING in RAW264.7 cells. Consistent with the fact that AML cells express undetectable level of STING (FIG. 3C), direct treatment of the hepatocytes with DMXAA does not inhibit HBV DNA replication. Conditioned media harvested from DMXAA-treated RAW264.7 cells, however, inhibits HBV DNA replication in the mouse hepatocytes in a dose-dependent manner (FIG. 3D).

Example 5

DMXAA-Induced Antiviral Response Reduced the Amount of Cytoplasmic HBV Capsids

In order to map the HBV replication step(s) being inhibited by DMXAA-induced antiviral response in macrophages, AML12HBV10 cells were treated with conditioned media harvested from TLR agonist- or DMXAA-treated RAW264.7 cells. Briefly, AML12HBV10 cells cultured in absence of tetracycline for 1 day were either directly treated with indicated concentrations of DMXAA, poly I:C, Pam3CSK4 or indirectly treated with 50% of conditioned media harvested from RAW264.7 cells (treated with the indicated concentrations of DMXAA or TLR agonists for 12 h). The AML12HBV10 cells were harvested 2 days after treatment for the following analysis: (FIG. 4A) Intracellular HBV RNA was determined by Northern blot (pgRNA, pre-genomic RNA, envRNAs, viral mRNAs specifying envelope proteins. 18S ribosomal RNA (rRNA) served as loading controls); (FIG. 4B) HBV core protein was determined by Western blot assay using total cell lysate ($\beta$-actin served as a loading control); the amounts of HBV capsids (FIG. 4C) and capsid-associated HBV DNA (FIG. 4D) were determined by a native agarose gel assay; and (FIG. 4E) Cytoplasmic HBV core DNA was determined by Southern blot hybridization.

Figure 4:
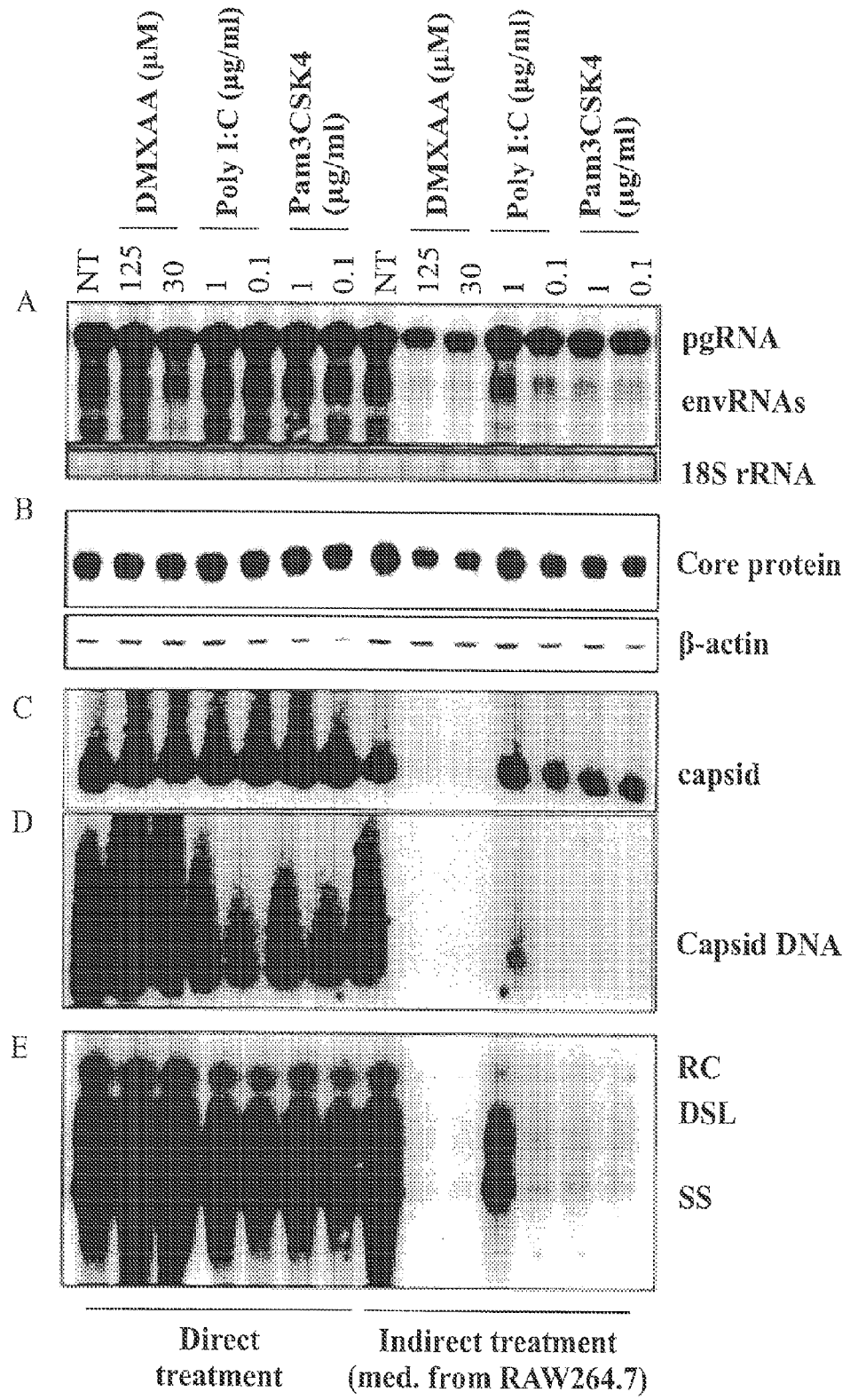
FIG. 4, comprising

As shown in FIG. 4, the antiviral response induced by DMXAA, and to lesser extents by TLR1/2 and TLR3 agonists in macrophages, post-transcriptionally reduced the amounts of HBV capsid protein and to a greater extent, the assembled capsids (FIGS. 4A, B and C). Consequentially, the amounts of HBV DNA replication intermediates were also decreased (FIGS. 4D and E).

Example 6

DMXAA Induces a Distinct Profile of Cytokine Response

To determine the antiviral mechanism of the conditioned media harvested from the DMXAA-treated RAW264.7, the signaling pathway activation and cytokine profiles induced by DMXAA as well as representative TLR agonists in treated RAW264.7 was analyzed.

Figure 5:
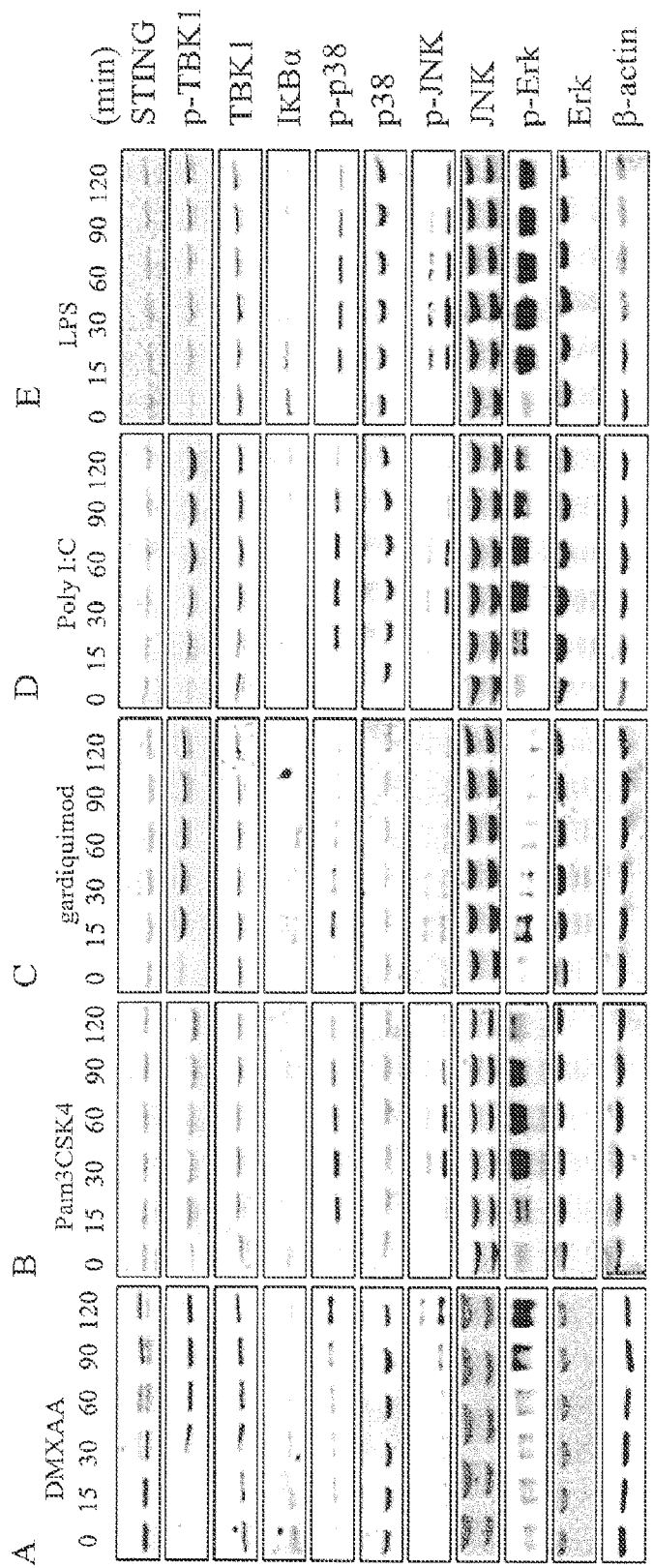
FIG. 5, comprising
Figure 6C:
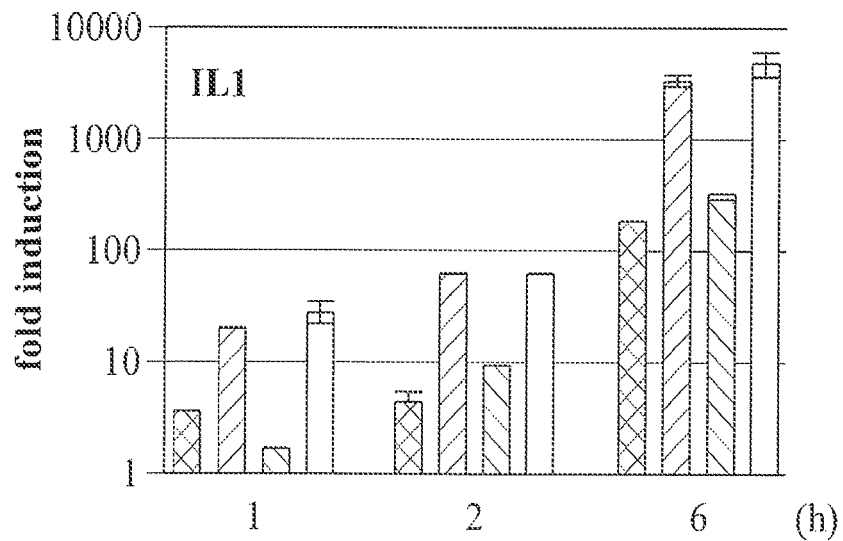
Figure 6D:
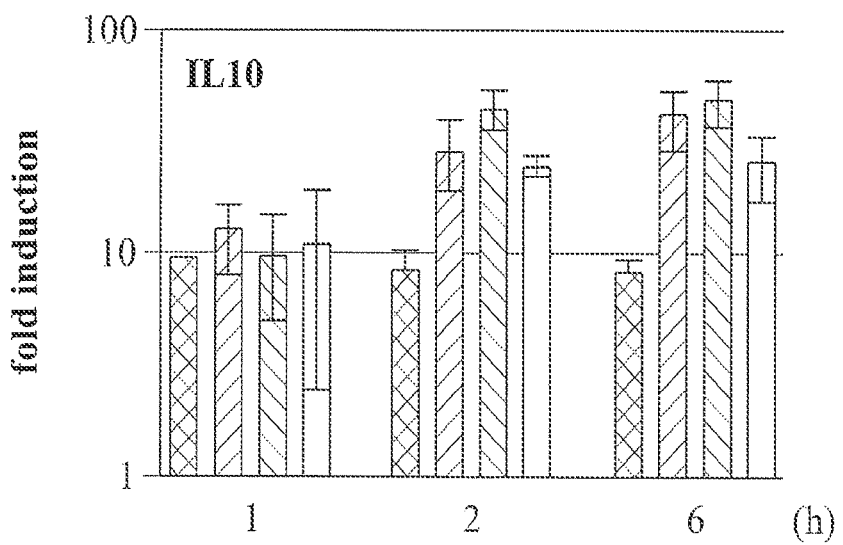
Figure 6E:
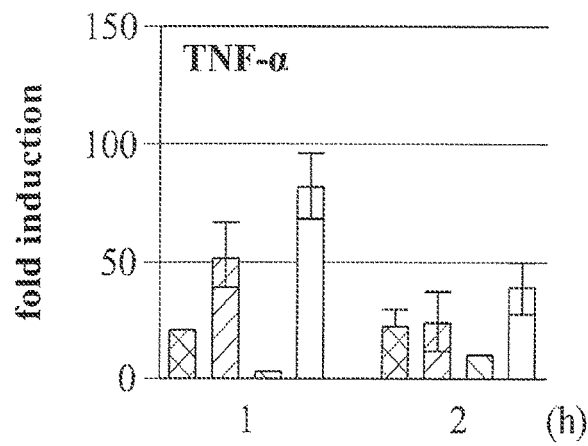
Figure 6F:
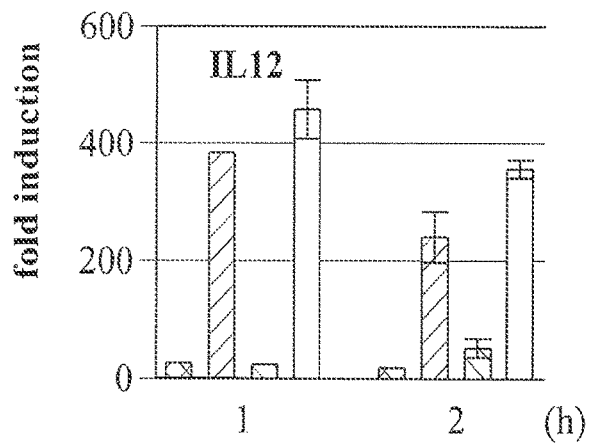
Figure 6G:
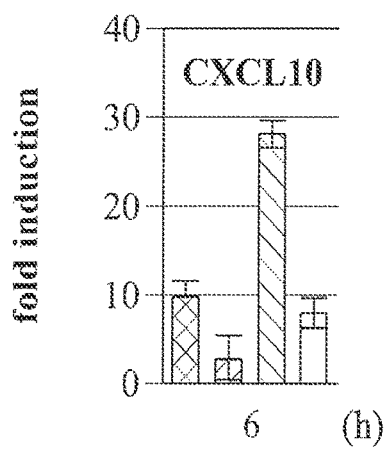

RAW264.7 cells were treated with 125 $\mu$M of DMXAA, 1 $\mu$g/ml of Pam3CSK4 (TLR1/2 agonist), 10 $\mu$g/ml of poly I:C (TLR3 agonist), 1 $\mu$g/ml of LPS (TLR4 agonist) or 3 $\mu$M of gardiquimod (TLR7 agonist) for the indicated times (FIG. 5). Total cellular proteins were fractioned by SDS-PAGE and transferred onto PVDF membranes. Total and phosphorylated STING, TBK1, p38, JNK and Erk as well as IkB-$\alpha$ were detected by Western blot assays with their specific antibodies. $\beta$-actin served as a loading control.

As shown in FIG. 5, only DMXAA, but not the agonists of TLR1/2, TLR7, TLR3 or TLR4, induced STING phosphorylation, which was detectable in cells treated with DMXAA for more than 30 min. However, DMXAA as well as all the tested TLR agonists efficiently induced phosphorylation of TBK1, a kinase essential for IRF3 phosphorylation and induction of IFN-$\beta$ in both STING and TLR pathways. Also, DMXAA and all tested TLR agonists induced degradation of IkB$\alpha$. Interestingly, while the activation of all three MAPK pathways, as demonstrated by the increase of the phosphorylated p38$\alpha$, JNK and ERK, was evident as early as 15 min in the cells treated with any one of the four TLR agonists, activation of the MAPK pathways was delayed and only became detectable at 90 min after DMXAA treatment.

The cytokine profiles induced by DMXAA and TLR agonists in RAW264.7 cells were determined by qRT-PCR assays (FIG. 6). RAW264.7 cells were treated with 125 $\mu$M of DMXAA, 1 $\mu$g/ml of Pam3CSK4 (TLR1/2 agonist), 10 $\mu$g/ml of poly I:C (TLR3 agonist) or 3 $\mu$M of gardiquimod (TLR7 agonist) for the indicated times. (FIG. 6A-G). The amounts of mRNA specifying the specific cytokines and chemokines were quantified by real-time RT-PCR assays. Data (mean±standard deviation, N=3) were expressed as fold induction of gene expression relative to untreated controls.

As shown in FIG. 6, qRT-PCR assays revealed that in comparison with the representative TLR agonists, DMXAA induced a predominant IFN response, but less vigorous inflammatory cytokine response. DMXAA induced approximately 100-fold more IFN-$\beta$ mRNA expression than that of TLR1/2, TLR3 or TLR7 agonists at 2 h post treatment (FIG. 6A). On the contrary, compared to DMXAA, the tested TLR agonists generally induced stronger expression of proinflammatory cytokines (FIGS. 6B to 6F) and chemokine (FIG. 6G) expression. The weaker cytokine response by DMXAA might be, at least in part, due to its slower and weaker activation of MAPK pathways. Interestingly, both TLR agonists- and DMXAA-induced IFN-$\beta$ response peaks at 2 h of treatment, but the inflammatory cytokine response (IL-1 and IL-10) peaks at 6 h of treatment or even later.

Example 7

Type I IFNs are the Primary Mediators of DMXAA-Induced Antiviral Response Against HBV The results presented above indicate that TLR agonists and DMXAA induce quantitatively different cytokine response at distinct kinetics. To determine the role of type I IFNs and other cytokines in DMXAA-induced antiviral response, it was investigated whether blockade of type I IFN response with a monoclonal antibody that specifically recognizes type I IFN receptor would attenuate the antiviral activity induced by DMXAA in macrophages.

Figure 7B:
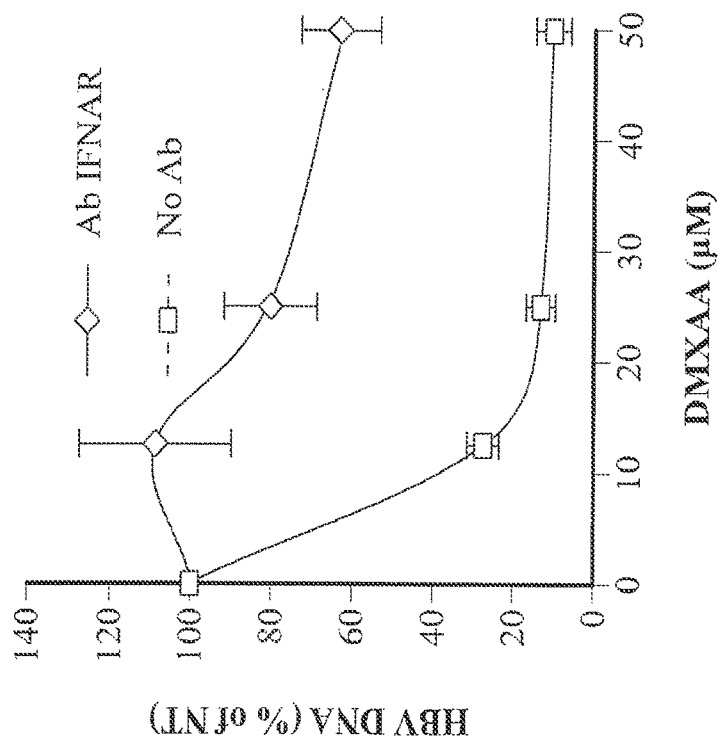
FIGS. 7A-7C, represents an exemplary RT-PCR analysis of AML12HBV10 cells pre-incubated with (circles) or without (squares) monoclonal antibody against type I interferon receptor IFNAR1 (Ab INFAR), followed by treatment with A) mIFN-α or B) 50% of conditioned media harvested from RAW264.7 cells treated with DMXAA. Data (mean±standard deviation, N=4) are presented as percentage of mock-treated controls (NT). C) AML12HBV10 cells treated with IL-1, IL-6 or TNF-α. Cytoplasmic HBV core DNA was analyzed by Southern blot hybridization.

AML12HBV10 cells cultured in absence of tetracycline for 1 day, were incubated either with or without 10 $\mu$g/ml of a monoclonal antibody against type I interferon receptor IFNAR1 (Ab INFAR) at 37° C. for 1 h, followed by treatment for 2 days with the indicated concentrations of mIFN-$\alpha$ (FIG. 7A) or 50% of conditioned media harvested from RAW264.7 cells (treated with the indicated concentrations of DMXAA for 12 h) (FIG. 7B). Cytoplasmic HBV DNA were quantified by a real-time PCR assay and data (mean±standard deviation, N=4) were presented as percentage of mock-treated controls (NT). AML12HBV10 cells cultured in the absence of tetracycline were treated with the indicated concentrations of IL-1, IL-6 or TNF-$\alpha$ for 4 days (FIG. 7C). Cytoplasmic HBV core DNA was analyzed by Southern blot hybridization.

Figure 7A:
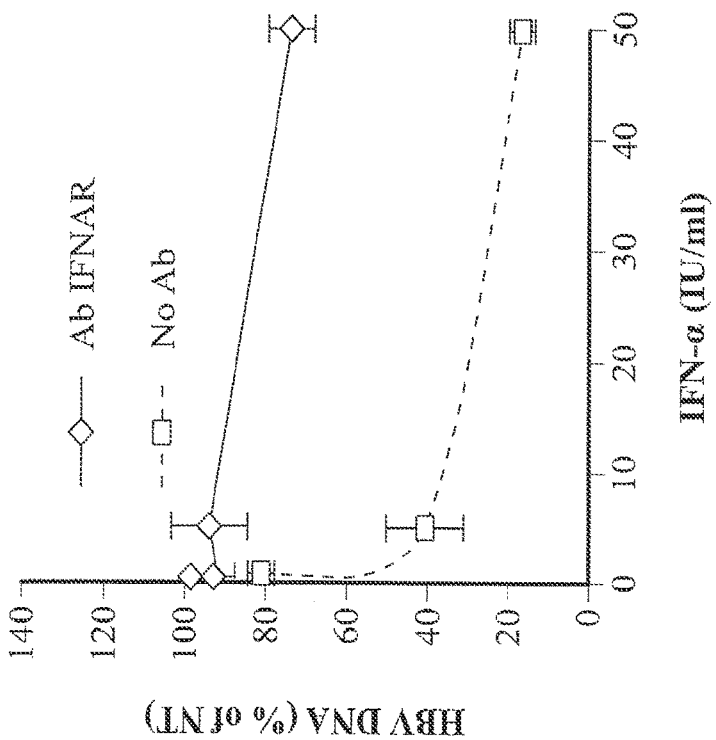
Figure 7C:
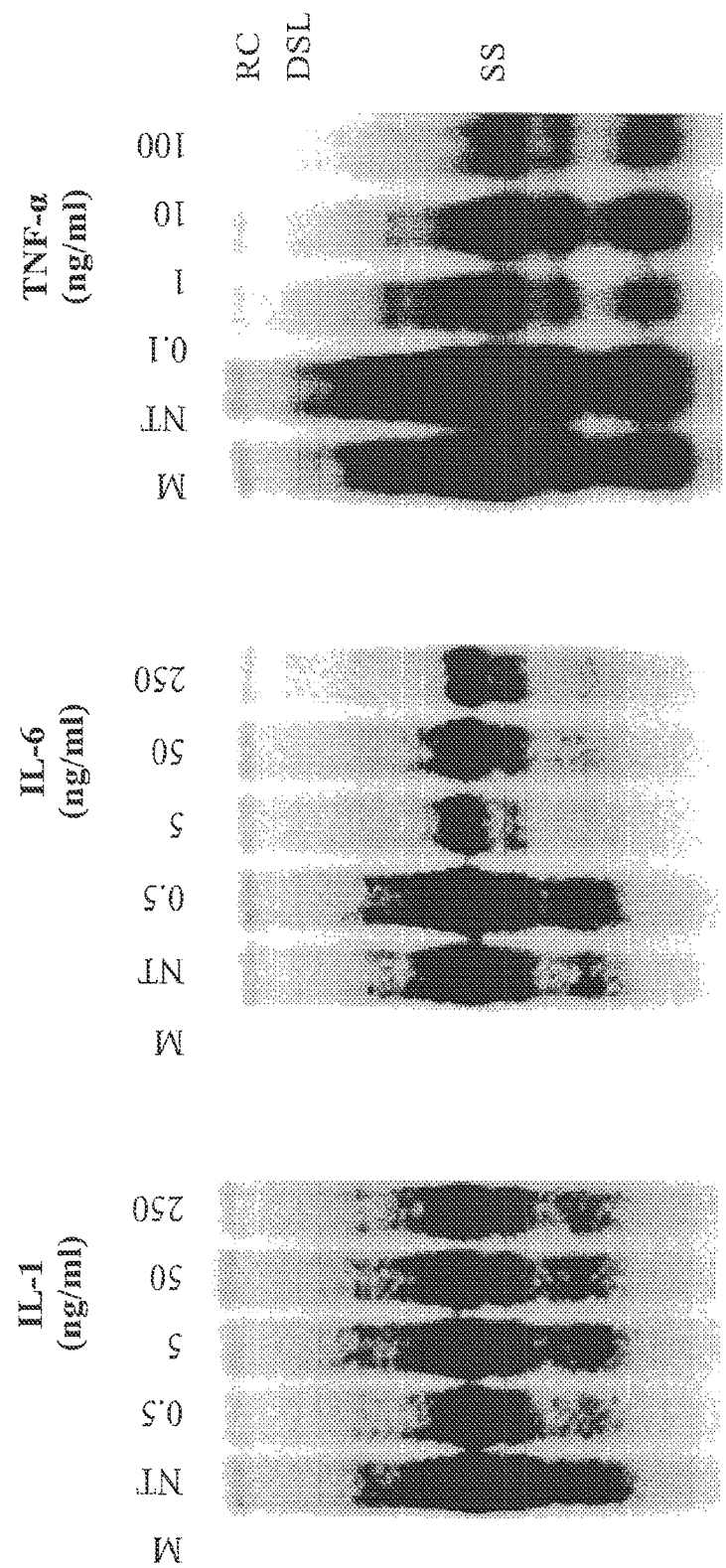

As shown in FIG. 7A, blockade of type I IFN receptor in AML12HBV10 cells significantly reduced the antiviral response by IFN-$\alpha$. Treatment of AML12HBV10 cells with the type I IFN receptor antibody also significantly attenuated the antiviral response by conditioned media from DMXAA-treated RAW264.7 cells (FIG. 7B), suggesting that type I IFNs are likely to be the primary mediators of DMXAA-induced antiviral response against HBV.

To determine the role of other cytokines in DMXAA-induced antiviral response, the antiviral effects of IL-1, IL-6 and TNF-$\alpha$ were tested. As shown in FIG. 7C, only TNF-$\alpha$ inhibited HBV DNA replication and may thus also play a role in DMXAA-induced antiviral response against HBV. This result is consistent with the fact that anti-TNF therapy of rheumatoid arthritis, inflammatory bowel diseases and psoriasis reactivates HBV infection in inactive carriers and suggests that TNF-α plays an important role in immune control of HBV infection in humans.

Example 8

DMXAA Induced Cytokine and Antiviral Responses are STING-Dependent

As shown above, DMXAA treatment of RAW264.7 cells activated STING and induced an antiviral cytokine response that suppresses HBV replication in mouse hepatocytes. To further determine the role of STING in DMXAA-induced antiviral cytokine response, RAW264.7-derived stable cell lines expressing either a scramble shRNA or shRNA specifically targeting STING mRNA were established.

Figures 8A, 8B:
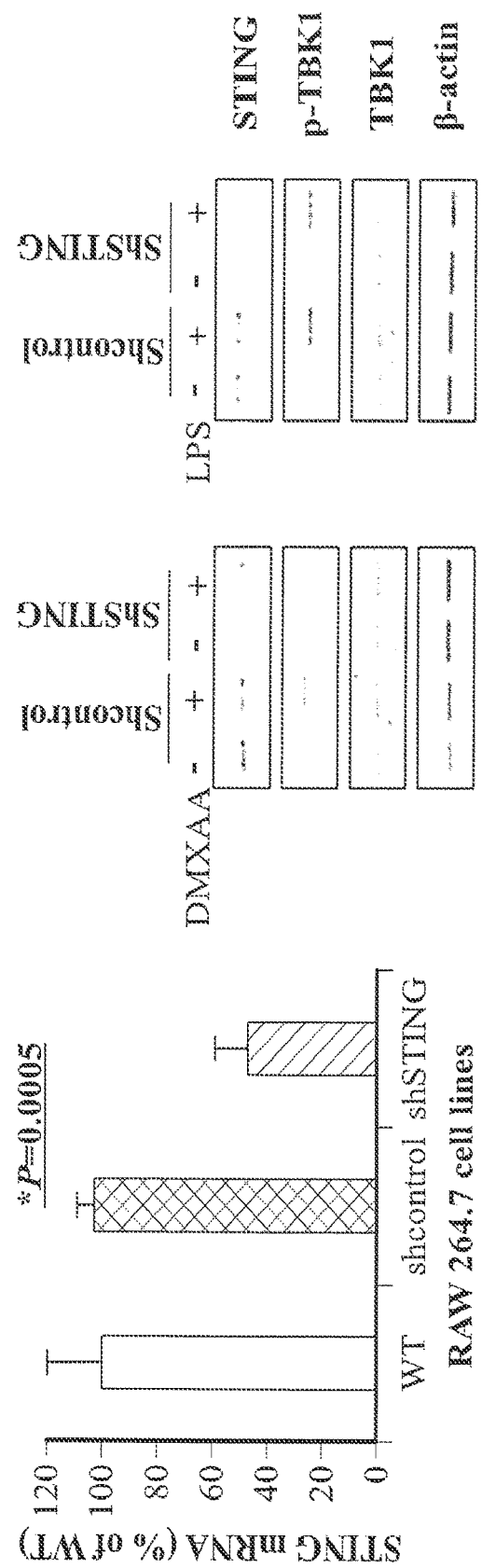
FIGS. 8A-8D, represents an exemplary analysis of: A) total RNAs extracted from parental RAW264.7 cells (WT) and RAW264.7-derived stable cell lines that express a scrambled shRNA (shcontrol) or shRNA targeting mouse STING mRNA (shSTING). STING mRNA levels were determined by real-time RT-PCR and data (mean±standard deviation, N=3) were expressed as the percentage of the STING mRNA in WT RAW264.7 cells. B) RAW264.7 cell lines expressing shcontrol or shSTING were mock-treated or treated with 125 µM of DMXAA for 30 min. Expression and activation of STING and TBK1 were determined by Western blot assays. Cells treated with 1 µg/ml of LPS served as controls. β-actin served as loading control. C) Knockdown of STING abrogated the DMXAA-induced IFN-β gene expression. RAW264.7-derived shcontrol and shSTING cell lines were treated with 125 µM of DMXAA for 3 h. IFN-β mRNA was quantified by a real time RT-PCR assay. Data (mean±standard deviation, N=3) were expressed as fold induction of gene expression relative to untreated controls. D) Knockdown of STING compromised DMXAA-induced antiviral activity. AML12HBV10 cells cultured in absence of tetracycline for 1 day were mock-treated or treated for 2 days with 50% of conditioned media harvested from RAW264.7-derived shcontrol or shSTING cells treated with DMXAA, LPS or Gardiquimod for 12 h. Cytoplasmic HBV core DNA was extracted and quantified by a real time PCR assay. AML12HBV10 cells treated with conditioned media from mock treated RAW267.4 cells served as control (NT). HBV DNA levels (mean±standard deviation, N=3) were expressed as percentage relative to NT control. Data were statistically analyzed by student's t-test. * indicates P<0.05.
Figures 8C, 8D:
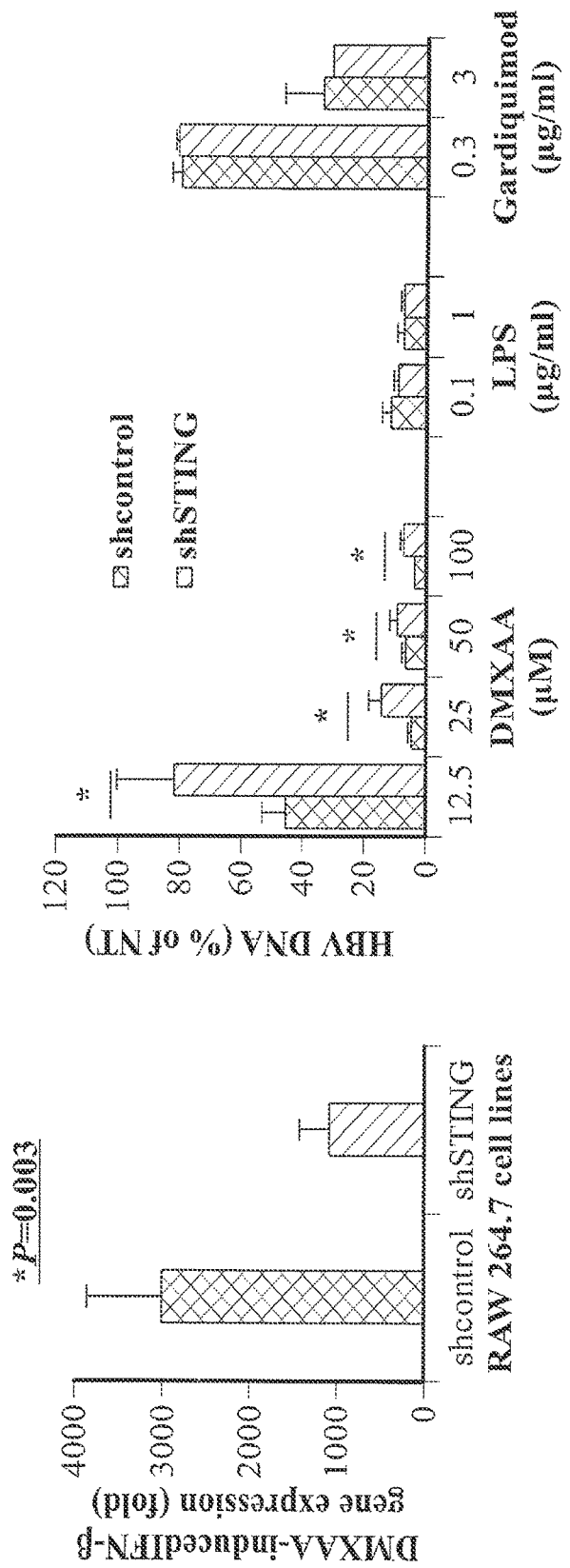

Total RNAs were extracted from parental RAW264.7 cells (WT) and RAW264.7-derived stable cell lines that express a scrambled shRNA (shcontrol) or shRNA targeting mouse STING mRNA (shSTING). STING mRNA levels were determined by real-time RT-PCR and data (mean±standard deviation, N=3) were expressed as the percentage of the STING mRNA in WT RAW264.7 cells (FIG. 8A). RAW264.7 cell lines expressing shcontrol or shSTING were mock-treated or treated with 125 μM of DMXAA for 30 min. Expression and activation of STING and TBK1 were determined by Western blot assays. Cells treated with 1 μg/ml of LPS served as controls. β-actin served as loading control (FIG. 8B). Knockdown of STING abrogated the DMXAA-induced IFN-β gene expression. RAW264.7-derived shcontrol and shSTING cell lines were treated with 125 μM of DMXAA for 3 h. IFN-β mRNA was quantified by a real time RT-PCR assay. Data (mean±standard deviation, N=3) were expressed as fold induction of gene expression relative to untreated controls (FIG. 8C). Knockdown of STING compromised DMXAA-induced antiviral activity. AML12HBV10 cells cultured in absence of tetracycline for 1 day were mock-treated or treated for 2 days with 50% of conditioned media harvested from RAW264.7-derived shcontrol or shSTING cells, which were treated with the indicated concentrations of DMXAA, LPS or Gardiquimod for 12 h. Cytoplasmic HBV core DNA was extracted and quantified by a real time PCR assay. AML12HBV10 cells treated with conditioned media from mock treated RAW267.4 cells served as control (NT). HBV DNA levels (mean±standard deviation, N=3) were expressed as percentage relative to NT control (FIG. 8D). Data were statistically analyzed by student's t-test. * indicates P<0.05.

Reduction of STING mRNA and protein expression in the cells expressing STING-specific shRNA was validated by qRT-PCR (FIG. 8A) and Western blot assay (FIG. 8B), respectively. DMXAA-induced, but not LPS-induced, TBK-1 activation was significantly compromised in RAW264.7 cells expressing STING mRNA-specific shRNA (FIG. 8B). Moreover, DMXAA-induced IFN-β expression (FIG. 8C) and antiviral activity against HBV (FIG. 8D) were significantly attenuated in the STING knockdown cells. These results thus suggest that DMXAA-induced antiviral cytokine response is indeed STING dependent.

Example 9

DMXAA Potently Inhibited HBV Replication in Mice

To further validate the antiviral effects of DMXAA in vivo, NOD/SCID mice were hydrodynamically injected with HBV 1.3mer plasmid to establish HBV replication in hepatocytes. Seven days post hydrodynamic injection of HBV 1.3mer plasmid, mice were either treated with a single dose of DMXAA at 25 mg/kg or vehicle, through intraperitoneal injection. (FIG. 9A) Twenty-four hours post treatment, HBV core DNA was extracted from livers and analyzed by a real-time PCR assay. Ten mice were included in control group and nine mice were included in treat group. Plots represent HBV DNA copies/ml from each animal after subtraction of the copies from input plasmid. (FIGS. 9B and 9C) Total RNA was extracted from livers and mRNA levels of OAS1b and viperin were analyzed by real-time RT-PCR assay. Plots represent mRNA levels from each animal. All the data were presented in boxplots to indicate medians, interquartiles as well as ranges (min, max), and were statistically analyzed by student's t-test (P<0.05).

As shown in FIG. 9A, compared to vehicle-treated control group, a single dose DMXAA treatment reduced intrahepatic HBV core DNA by 1.3-log at 24 h after treatment. In agreement with the anticipated antiviral mechanism, expression of representative IFN-stimulated genes (ISGs), such as OAS1b and viperin, was significantly induced in the livers of DMXAA treated animals (FIGS. 9B and 9C). Noticeably, the average body weight of DMXAA-treated mice reduced by approximately 8% (data not shown).

Example 10

Activation of Human STING Pathway and Antiviral Effect in Human Hepatoma Cells

Figures 10A, 10B:
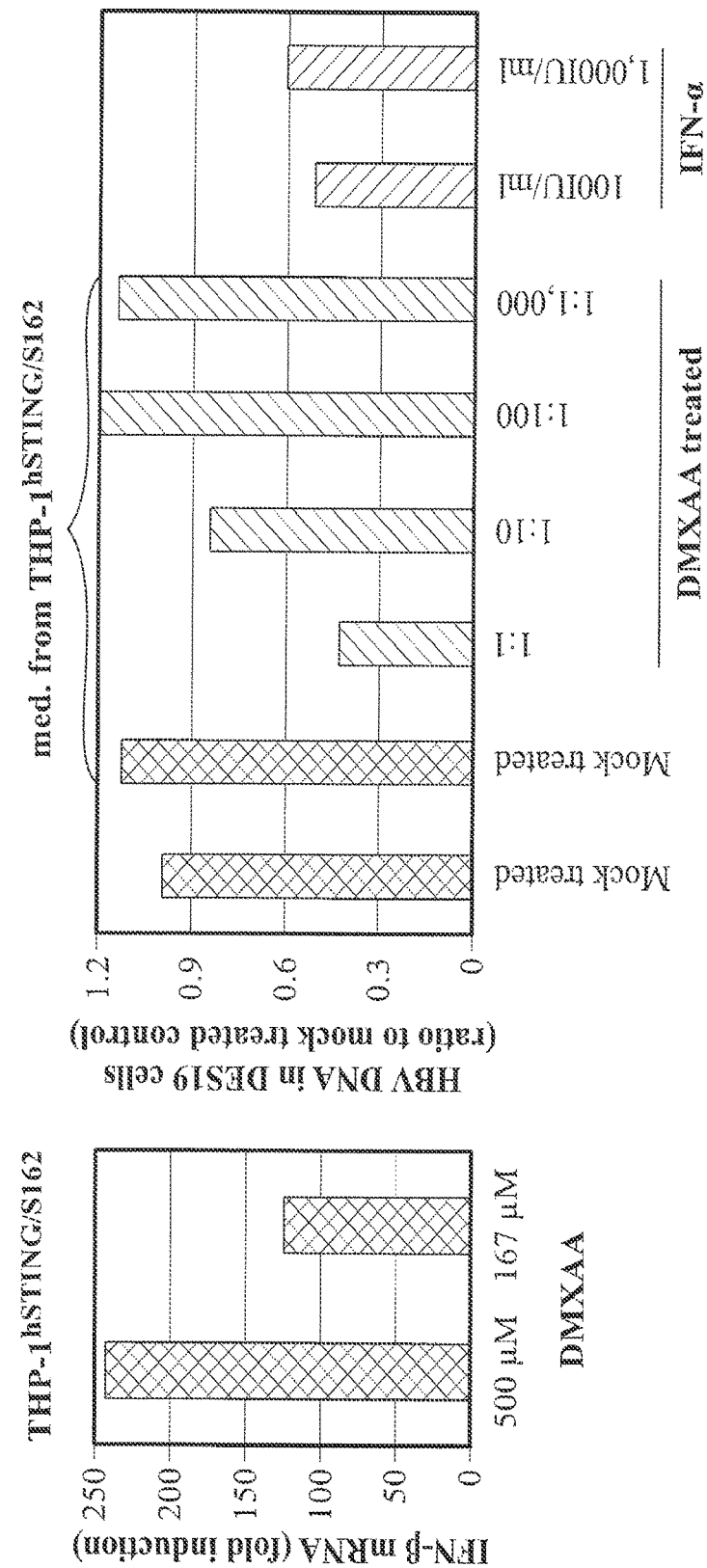
FIGS. 10A-10B, represents an exemplary analysis of the activation of human STING pathway induced cytokine response in THP-1 cells and antiviral effect in human hepatoma cells. A) mRNA expression levels of IFN-β from THP-1hSTINGS162 cells expressing the S162A mutant form of human STING treated with DMXAA for 2 hrs. Data (mean±standard deviation, N=3) is expressed as relative gene expression after normalization to untreated controls (fold). B) DES19 cells treated with supernatants from THP-1hSTINGS162 cells treated with DMXAA for 12 hrs. HBV DNA expression levels (means±standard deviations, N=3) were expressed as percentage relative to mock treated control. DES19 cells treated with IFN-α served as positive control.

In order to validate the results obtained in mouse macrophage-hepatocyte system, a human monocyte THP1-derived cell line expressing a human STING with S162A mutation (hSTING/S162) was established to confer sensitivity to DMXAA. To analyze the activation of human STING pathway on cytokine response in THP-1 cells and the antiviral effect in human hepatoma cells, THP-1hSTINGS162 cells expressing S162A mutant form of human STING were treated with DMXAA for 2 hrs. Total cellular RNA was extracted to detect mRNA expression levels of IFN-β by real time RT-PCR. Data (mean±standard deviation, N=3) were expressed as relative gene expression after normalization to untreated controls (fold) (FIG. 10A). Additionally, THP-1hSTINGS162 cells were treated with DMXAA for 12 hrs, conditioned medium with indicated dilution were then transferred to DES19, a human hepatoma cell line harboring HBV replication. HBV core DNA was extracted 6 days post treatment, and quantified by real time PCR assay. HBV DNA expression levels (means±standard deviations, N=3) were expressed as percentage relative to mock treated control. DES19 cells treated with IFN-α served as positive control (FIG. 10B).

DMXAA treatment of THP1-hSTING/S162 cells induced robust IFN-β expression (FIG. 10A). Moreover, the conditioned media from DMXAA-treated THP1-hSTING/S162 cells efficiently suppressed HBV replication in human hepatoma cells (HepDES19) supporting HBV replication (FIG. 10B). Thus, activation of human STING in human monocytes induces a robust cytokine response to inhibit HBV replication in human hepatoma cells.

The work presented herein demonstrates for the first time that activation of STING pathway with STING agonists induces a cytokine response in macrophages (and also potentially liver NPCs) that in turn potently inhibits HBV replication in hepatocytes.

Detailed characterization of the antiviral cytokine responses induced by TLR and STING agonists revealed distinct characteristics. Specifically, DMXAA induced a delayed activation of MAPK pathways. DMXAA induced a cytokine response in macrophages that was dominated by IFN-β and demonstrated a more potent antiviral activity against HBV in hepatocytes. Additionally, DMXAA induced a less vigorous proinflammatory cytokine response compared to TLR agonists. Accordingly, if considering only the property of inducing non-cytolytic antiviral cytokine response, intrahepatic activation of STING pathway seems to be superior to that activation of TLR pathways. STING agonist's induction of a more potent antiviral response and a less pro-inflammatory cytokine response may result in less inflammation and tissue damage. Hence, intrahepatic activation of STING may be an ideal therapeutic approach to treat chronic hepatitis B. This therapeutic approach should provide more efficacious, sustained suppression of HBV and could potentially be curative, which is rarely achieved by the current FDA-approved therapeutics against hepatitis B. This represents a novel therapeutic concept and approach for chronic hepatitis B.

The above results demonstrated that STING is a potential target for immunotherapy of chronic hepatitis B. Side-effects associated with systemic administration of TLR agonist immunotherapies could be circumvented by targeted activation of STING pathway in liver macrophages or other non-parenchymal cells through liposomal delivery of STING agonists, which are primarily cleared from circulation by Kupffer cells.

Those skilled in the art will appreciate that numerous changes and modifications can be made to the preferred embodiments of the methods and that such changes and modifications can be made without departing from the spirit of the disclosed methods. It is, therefore, intended that the appended claims cover all such equivalent variations as fall within the true spirit and scope of the methods.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1

A method of treating a subject having a hepatitis B viral infection, comprising administering an effective amount of a STING agonist to said subject.

Embodiment 2

The method of Embodiment 1, wherein said STING agonist stimulates an innate cytokine response in macrophages, dendritic cells, liver non-parenchymal cells, or any combination thereof.

Embodiment 3

The method of Embodiment 2, wherein said innate cytokine response is mediated through cytokines.

Embodiment 4

The method of Embodiment 3, wherein said innate cytokine response is mediated through type 1 interferon.

Embodiment 5

The method of any one of the previous Embodiments, wherein said STING agonist comprises a flavonoid.

Embodiment 6

The method of Embodiment 5, wherein said flavonoid comprises 10-(carboxymethyl) 9(10H)acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof.

Embodiment 7

The method of Embodiment 6, wherein said flavonoid comprises DMXAA.

Embodiment 8

The method of any one of the previous Embodiments, wherein said STING agonist suppresses hepatitis B virus replication in infected hepatocytes.

Embodiment 9

The method of Embodiment 8, wherein said STING agonist reduces hepatitis B virus capsid levels.

Embodiment 10

A method of identifying compounds useful in the treatment of hepatitis B virus infection comprising: treating liver resident dendritic cells, macrophages, nonparenchymal cells, or any combination thereof with a compound of interest; incubating the treated cells in a conditioned medium; removing the conditioned medium or a portion thereof from the treated cells; and incubating hepatitis B virus infected hepatocytes with the conditioned medium.

Embodiment 11

The method of Embodiment 10, further comprising measuring hepatitis B virus replication.

Embodiment 12

The method of any one of Embodiments 10 or 11, wherein the treating step stimulates an innate cytokine immune response within the liver resident dendritic cells, macrophages, nonparenchymal cells, or any combination thereof, and release of cytokines into the conditioned medium.

Embodiment 13

The method of Embodiment 12, wherein the cytokines include but are not limited to Type I interferons.

Embodiment 14

The method of any one of Embodiments 10 to 13, wherein the conditioned medium suppresses hepatitis B replication in the infected hepatocytes.

Embodiment 15

A method of treating a subject having a hepatitis B virus infection, comprising: treating liver resident dendritic cells, macrophages, nonparenchymal cells, or any combination thereof with a compound of interest; incubating the treated cells in a conditioned medium; removing the conditioned medium or a portion thereof from the treated cells; and administering the conditioned medium or a portion thereof to said subject.

Embodiment 16

The method of Embodiment 15, wherein said compound of interest comprises one or more STING agonists.

Embodiment 17

The method of Embodiment 16, wherein said STING agonist comprises a flavonoid.

Embodiment 18

The method of Embodiment 17, wherein said flavonoid comprises 10-(carboxymethyl)-9(10H) acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof.

Embodiment 19

The method of Embodiment 18, wherein said flavonoid comprises DMXAA.

Embodiment 20

The method of any one of Embodiments 15 to 19, wherein the liver resident dendritic cells, macrophages, nonparenchymal cells, or any combination thereof are human cells.

Embodiment 21

The method of any one of Embodiments 15 to 20, wherein the human liver resident dendritic cells, macrophages, nonparenchymal cells, or any combination thereof are modified to express a mutant STING.

Embodiment 22

The method of Embodiment 21, wherein the human liver resident dendritic cells, macrophages, nonparenchymal cells, or any combination thereof are transfected or transformed with a mutant STING prior to the treating step.

Embodiment 23

The method of any one of Embodiments 21 or 22, wherein the mutant STING is STING S162A.

Embodiment 24

The method of any one of Embodiments 15-23, wherein the liver resident dendritic cells, macrophages, nonparenchymal cells, or any combination thereof are autologous cells.

---

What is claimed:

1. A method of treating a hepatitis B viral (HBV) infection in a subject, the method comprising administering a pharmaceutically effective amount of a STING agonist to the subject, wherein the STING agonist comprises at least one selected from the group consisting of 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, and any combinations thereof.

2. The method of claim 1, wherein the STING agonist stimulates an innate cytokine response in at least one cell from the subject, wherein the cell is selected from the group consisting of macrophage, dendritic cell, liver non-parenchymal cell, and any combinations thereof.

3. The method of claim 2, wherein the innate cytokine response is mediated through cytokines in the subject.

4. The method of claim 3, wherein the innate cytokine response is mediated through type 1 interferon in the subject.

5. The method of claim 1, wherein the STING agonist comprises DMXAA.

6. The method of claim 1, wherein the STING agonist suppresses hepatitis B virus replication in infected hepatocytes in the subject.

7. The method of claim 6, wherein the STING agonist reduces hepatitis B virus capsid levels in the subject.

8. A method of identifying a compound useful in treating hepatitis B virus (HBV) infection, the method comprising:
   treating at least one cell selected from the group consisting of liver resident dendritic cell, macrophage, non-parenchymal cell, and any combination thereof with a test compound, thereby generating a treated cell;
   incubating the treated cell in a conditioned medium;
   separating the conditioned medium or a portion thereof from the treated cell; and
   incubating a HBV-infected hepatocyte with the conditioned medium or portion thereof, wherein, if the conditioned medium or portion thereof suppresses HBV replication in the HBV-infected hepatocyte, the test compound is identified as a compound useful in treating HBV infection.

9. The method of claim 8, further comprising measuring hepatitis B virus replication in the HBV-infected hepatocyte incubated with the conditioned medium or portion thereof.

10. The method of claim 8, wherein the treating step stimulates an innate cytokine immune response within the at least one cell with release of cytokines into the conditioned medium.

11. The method of claim 10, wherein the cytokine comprises a Type I interferon.

12. A method of treating a subject having a hepatitis B virus (HBV) infection in a subject, the method comprising:
   treating at least one cell selected from the group consisting of liver resident dendritic cell, macrophage, non-parenchymal cell, and any combinations thereof, with a compound, thus generating a treated cell;
   incubating the treated cell in a conditioned medium;
   separating the conditioned medium or a portion thereof from the treated cell; and
   administering the conditioned medium or portion thereof to the subject.

13. The method of claim 12, wherein the compound comprises at least one STING agonist.

14. The method of claim 13, wherein the at least one STING agonist comprises a flavonoid.

15. The method of claim 14, wherein the flavonoid comprises at least one selected from the group consisting of 10-(carboxymethyl) 9(10H)acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, and any combinations thereof.

16. The method of claim 14, wherein the flavonoid comprises DMXAA.

17. The method of claim 12, wherein the at least one cell is human.

18. The method of claim 12, wherein the at least one cell is modified to express a mutant STING.

19. The method of claim 18, wherein at least one cell is transfected or transformed with a mutant STING prior to the treating step.

20. The method of claim 18, wherein the mutant STING is STING S162A.

21. The method of claim 12, wherein the at least one cell is autologous to the subject.

22. A method of treating a hepatitis B viral (HBV) infection in a subject, the method comprising administering a pharmaceutically effective amount of a STING agonist to the subject, wherein the STING agonist is the only therapeutically effective agent administered to the subject.

23. The method of claim 22, wherein the STING agonist stimulates an innate cytokine response in at least one cell in the subject, wherein the cell is selected from the group consisting of macrophage, dendritic cell, liver non-parenchymal cell, and any combinations thereof.

24. The method of claim 22, wherein the STING agonist is a flavonoid.

25. The method of claim 24, wherein the flavonoid comprises at least one selected from the group consisting of 10-(carboxymethyl) 9(10H)acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone and any combinations thereof.

26. The method of claim 22, wherein the STING agonist suppresses hepatitis B virus replication in infected hepatocytes in the subject.

27. The method of claim 22, wherein the STING agonist reduces hepatitis B virus capsid levels in the subject.

* * * * *